(12) United States Patent
Altarac et al.

(10) Patent No.: US 10,368,923 B2
(45) Date of Patent: Aug. 6, 2019

(54) BONE FIXATION SYSTEM

(71) Applicant: NEUROSTRUCTURES, INC., Irvine, CA (US)

(72) Inventors: Moti Altarac, Irvine, CA (US); Joey Reglos, Lake Forest, CA (US)

(73) Assignee: NeuroStructures, Inc., Irvine, CA (US)

( * ) Notice: Subject to any disclaimer, the term of this patent is extended or adjusted under 35 U.S.C. 154(b) by 175 days.

(21) Appl. No.: 14/526,241

(22) Filed: Oct. 28, 2014

(65) Prior Publication Data
US 2016/0113682 A1  Apr. 28, 2016

(51) Int. Cl.
*A61B 17/70* (2006.01)

(52) U.S. Cl.
CPC ...... *A61B 17/7085* (2013.01); *A61B 17/7037* (2013.01)

(58) Field of Classification Search
CPC ............ A61B 17/7085; A61B 17/7086; A61B 17/7091; A61B 17/7037; A61B 17/7083; A61B 17/7077; A61B 17/708
See application file for complete search history.

(56) References Cited

U.S. PATENT DOCUMENTS

| | | | | |
|---|---|---|---|---|
| 8,439,924 B1 * | 5/2013 | McBride | ............ | A61B 17/7085 606/104 |
| 8,460,308 B2 * | 6/2013 | Marino | ............. | A61B 17/7002 606/104 |
| 9,743,958 B2 * | 8/2017 | Ishii | .................. | A61B 17/7032 |
| 2007/0167954 A1 * | 7/2007 | Sicvol | ................ | A61B 17/7032 606/104 |
| 2008/0051794 A1 * | 2/2008 | Dec | .................... | A61B 17/7091 606/250 |
| 2010/0312279 A1 * | 12/2010 | Gephart | ............. | A61B 17/3421 606/264 |
| 2011/0313477 A1 * | 12/2011 | McLean | ............. | A61B 17/7032 606/86 A |
| 2012/0109208 A1 * | 5/2012 | Justis | ................. | A61B 17/7032 606/264 |
| 2013/0046345 A1 * | 2/2013 | Jones | ................. | A61B 17/7037 606/266 |
| 2013/0060294 A1 * | 3/2013 | Donahue | ............ | A61B 17/8605 606/308 |
| 2013/0245705 A1 * | 9/2013 | McBride | ............ | A61B 17/7032 606/86 R |

(Continued)

*Primary Examiner* — Jacqueline T Johanas
(74) *Attorney, Agent, or Firm* — Rimas T. Lukas

(57) ABSTRACT

A bone fixation system is provided. The bone fixation system includes a receiver coupled to a bone fastener. The receiver includes an inner bore and channel that provides a seat for an elongate fixation rod. The inner surface of the receiver includes locations for an instrument to securely grasp the receiver from the inside of the receiver without obstructing the inner bore. The instrument is provided with hooks that uniquely grasp the receiver from the inside and outside of the receiver. The instrument also includes flexible prongs configured to engage recesses formed in the outer surface of the receiver. The prongs have prong extensions that conform in shape to the recesses. The prongs and recesses have three separated perimeter surfaces each having a component perpendicular to the longitudinal axis. The bone fixation system provides a strong connection between the screw and the instrument for the demands unique to spinal surgery.

17 Claims, 19 Drawing Sheets

(56) References Cited

U.S. PATENT DOCUMENTS

| | | | |
|---|---|---|---|
| 2013/0261679 A1* | 10/2013 | McBride | A61B 17/7085 606/86 A |
| 2013/0331892 A1* | 12/2013 | Peterson | A61B 17/0218 606/279 |
| 2014/0142632 A1* | 5/2014 | Keyer | A61B 17/7037 606/265 |
| 2014/0277145 A1* | 9/2014 | Reitblat | A61B 17/162 606/250 |
| 2014/0277206 A1* | 9/2014 | Reitblat | A61B 17/7085 606/86 A |
| 2015/0039035 A1* | 2/2015 | Kruger | A61B 17/7037 606/264 |
| 2016/0022317 A1* | 1/2016 | Kraus | A61B 17/708 606/267 |

* cited by examiner

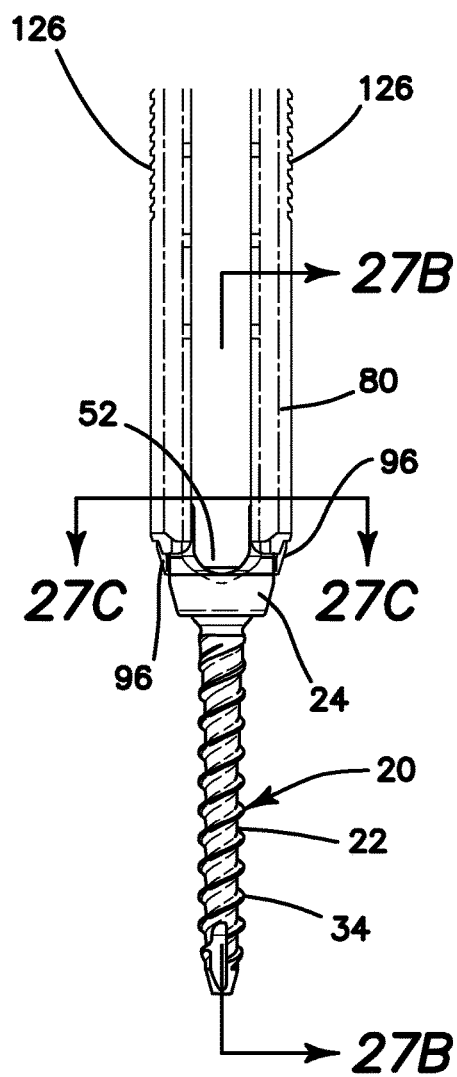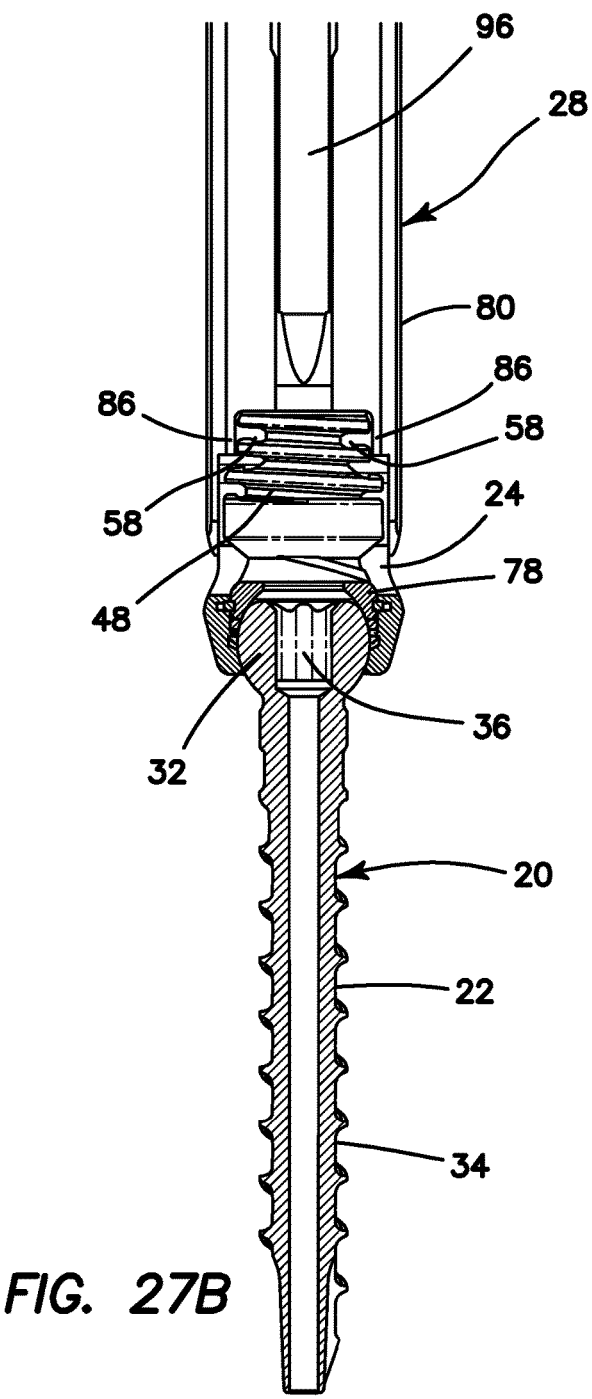
FIG. 27A
FIG. 27B

BONE FIXATION SYSTEM

FIELD OF THE INVENTION

The present invention is directed to surgical devices and methods, and in particular, to bone fixation systems used in spinal surgery.

BACKGROUND OF THE INVENTION

Spinal fusion is a common surgical procedure used to correct numerous disease states including degenerative disorders, trauma, instability, and deformity. An often used method of fusion entails the use of bone screws placed through various sections of the vertebral body including the body, pedicle, facets, lamina, lateral masses, and/or transverse processes. These screws are then linked rigidly with a rod, plate or other fixation device to immobilize the vertebral segments.

Typical spinal bone screws include a shank portion connected to an enlarged head portion also called a receiver or tulip. The shank portion includes external threads for insertion into bone. Self-tapping screws or screws that require pre-tapping are available. The head portion of the bone screw includes a U-shaped channel configured for receiving a stabilization rod. A rod is inserted into the channel and a set screw is threaded into the channel to secure one end of the rod to the screw. The other end of the rod is connected to a second bone screw inserted into an adjacent vertebral body. Thereby, the rod spans an intervertebral disc space to stabilize the motion segment. Multiple rods and screws can be employed for multi-level stabilization. The receiver portion of the screw is typically connected in a manner that permits angulation of the receiver relative to the shank portion. Due to the variation in a patient's anatomy and differences in screw placement technique, polyaxial or multi-axial bone screws allow for a variation in the angulation of the receiver portion relative to the shank portion in order to allow the receiver portion to more closely align for receiving a fixation rod within the channel of the receiver portion. Fixed receiver screws may also be employed.

To insert a bone screw, an insertion instrument is attached to the receiver portion of the screw and the insertion instrument and the screw are inserted through an incision. The incision may be small as in minimally invasive surgical procedures or in mini-open procedures or the incision may be large as in open surgical procedures. The clinician places the bone screw in the most optimum position with or without over-the-guidewire placement of a cannulated screw while checking correct alignment with the bony anatomy via fluoroscopic observation. Much skill is required and the clinician relies heavily on the proper functioning of instrumentation in the most difficult anatomical situations.

The bone screw insertion instrument is typically an elongated tower that connects to the screw at the distal end. If a polyaxial bone screw is employed with the insertion instrument, the insertion instrument must be able to lock the angulation of the head relative to the shank so that the screw is firmly inserted into the bone. Sometimes forces during the placement of the screw are so great that the insertion instrument is knocked off the screw. Typically, the insertion instrument includes two oppositely placed prongs that mate with recesses formed on the outer surface of the head. Sometimes, the prongs of the insertion instrument get hooked on adjacent anatomy and result in the insertion instrument detaching from the screw. Furthermore, because space is at a premium in the spinal anatomy, the head portion is typically designed to be as small as possible so that it does not protrude from the skin or impinge on adjacent anatomy after surgery. Although, the size of the implants is a major driving force in spinal bone screw design, the strength of spinal implants and instruments is extremely important. Generally, the contact area of the prongs of the insertion instrument with the recesses on the receiver as well as the depth of the recesses are as small as possible because of competing size and strength design considerations. As a result, the insertion instrument sometimes dislodges from the screw. Typically, the prongs of an insertion instrument are covered to close the prongs onto the receiver. Because the distal-most portion remains uncovered in order to navigate the insertion between crowded anatomy, the prongs may splay slightly outwardly especially under torsional forces undergone during screw placement which may result in the insertion instrument slipping off the screw. The receiver is connected to the distal end of the insertion instrument and the instrument is manipulated at the proximal end which results in amplification of the input force at the proximal end and a leveraged output force at the distal end of the instrument. Such angulation can result in the screw disconnecting from the insertion instrument. Other forces including torsional forces and pulling of the instrument may also dislodge the screw from the instrument. Precious time is lost when the clinician must re-attach the screw to the instrument and continue with the procedure. For all of these reasons, a strong need exists for an improved screw and instrument system that strengthens the connective interface between the screw and the insertion instrument under the demands of size and use restrictions unique to spinal surgery. The present invention provides such an improved bone screw and insertion instrument system.

SUMMARY OF THE INVENTION

According to one aspect of the invention, a bone fixation system is provided. The bone fixation system includes a bone fastener. The bone fastener includes a bone engaging portion and a head connected to the bone engaging portion. The bone fastener includes a receiver having a proximal end, a distal end and a longitudinal axis. The receiver further includes a sidewall extending between the proximal end and the distal end and has an inner surface and an outer surface. An inner bore extends between a top opening at the proximal end and a bottom opening at the distal end. The bone fastener is connected to the receiver such that the bone engaging portion extends through the bottom opening. The receiver includes two oppositely disposed arms defined by the sidewall and at least one rod channel is defined between the two arms. The at least one rod channel is interconnected with the top opening and the inner bore. The inner surface of each arm has a longitudinally extending interlocking or threaded surface located between two longitudinally extending smooth surfaces. Each smooth surface extends from the outer surface to the inner surface. The smooth surfaces are configured to engage with an insertion instrument.

According to another aspect of the invention, a bone fixation system is provided. The bone fixation system includes a bone fastener having a bone engaging portion and a head integrally connected to the bone engaging portion. The bone fixation system includes a receiver having a proximal end, a distal end and a longitudinal axis. The receiver has a sidewall extending between the proximal end and the distal end and has an inner surface and an outer surface. An inner bore extends between a top opening at the proximal end and a bottom opening at the distal end. The bone fastener is connected to the receiver such that the bone engaging portion extends through the bottom opening. The receiver includes two oppositely disposed arms defined by the sidewall and at least one rod channel defined between the two arms. The at least one rod channel is interconnected with the top opening and the inner bore. The inner surface of each arm has a longitudinally extending interlocking or threaded inner surface. The receiver includes recesses formed in the outer surface of each arm. Each recess extends inwardly from the outer surface to define a recessed surface having perimeter surface. The perimeter surface has a first proximal surface interconnected to a second proximal surface and a third proximal surface. The first proximal surface, second proximal surface and third proximal surface have a lateral dimension perpendicular to the longitudinal axis. One of the first proximal surface, second proximal surface and third proximal surface is spaced from at least one other of the first proximal surface, second proximal surface and third proximal surface along the longitudinal axis.

According to another aspect of the invention, a bone fixation system is provided. The bone fixation system includes bone fastener. The bone fastener includes a bone engaging portion and a head connected to the bone engaging portion. The bone fastener includes a receiver having a proximal end, a distal end and a longitudinal axis. The receiver includes a sidewall extending between the proximal end and the distal end and has an inner surface and an outer surface. An inner bore extends between a top opening at the proximal end and a bottom opening at the distal end. The bone fastener is connected to the receiver such that the bone engaging portion extends through the bottom opening. The receiver includes a first arm oppositely disposed from a second arm. The first and second arms are defined by the sidewall. At least one rod channel is defined between the two arms. The at least one rod channel is interconnected with the top opening and the inner bore. The inner surface of each arm has two flat surfaces interconnected by a longitudinally extending threaded surface. The flat surfaces are located near the proximal end of the receiver. The bone fixation system further includes an instrument comprising an elongate tower having a central lumen extending between a proximal end and an open distal end. The distal end of the tower has four hooks. Two of the hooks are configured to contact the two flat surfaces on the first arm and the other two hooks are configured to contact the two flat surfaces on the second arm, thereby, grasping the receiver from the inner surface. The instrument also gasps the receiver from at least one other location at the outer surface at each arm.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary the dimensions of the various features are arbitrarily expanded or reduced for clarity. Included in the drawings are the following figures:

FIG. 19 is a sectional, detailed view of the distal end of the instrument in FIG. 18 according to the present invention.

FIG. 27A is a partial side elevational view of an instrument and bone fixation system according to the present invention.

FIG. 27B is a cross-sectional view taken along line 27B-27B of FIG. 27A of an instrument and bone fixation system according to the present invention.

DETAILED DESCRIPTION OF THE INVENTION

Figure 1:
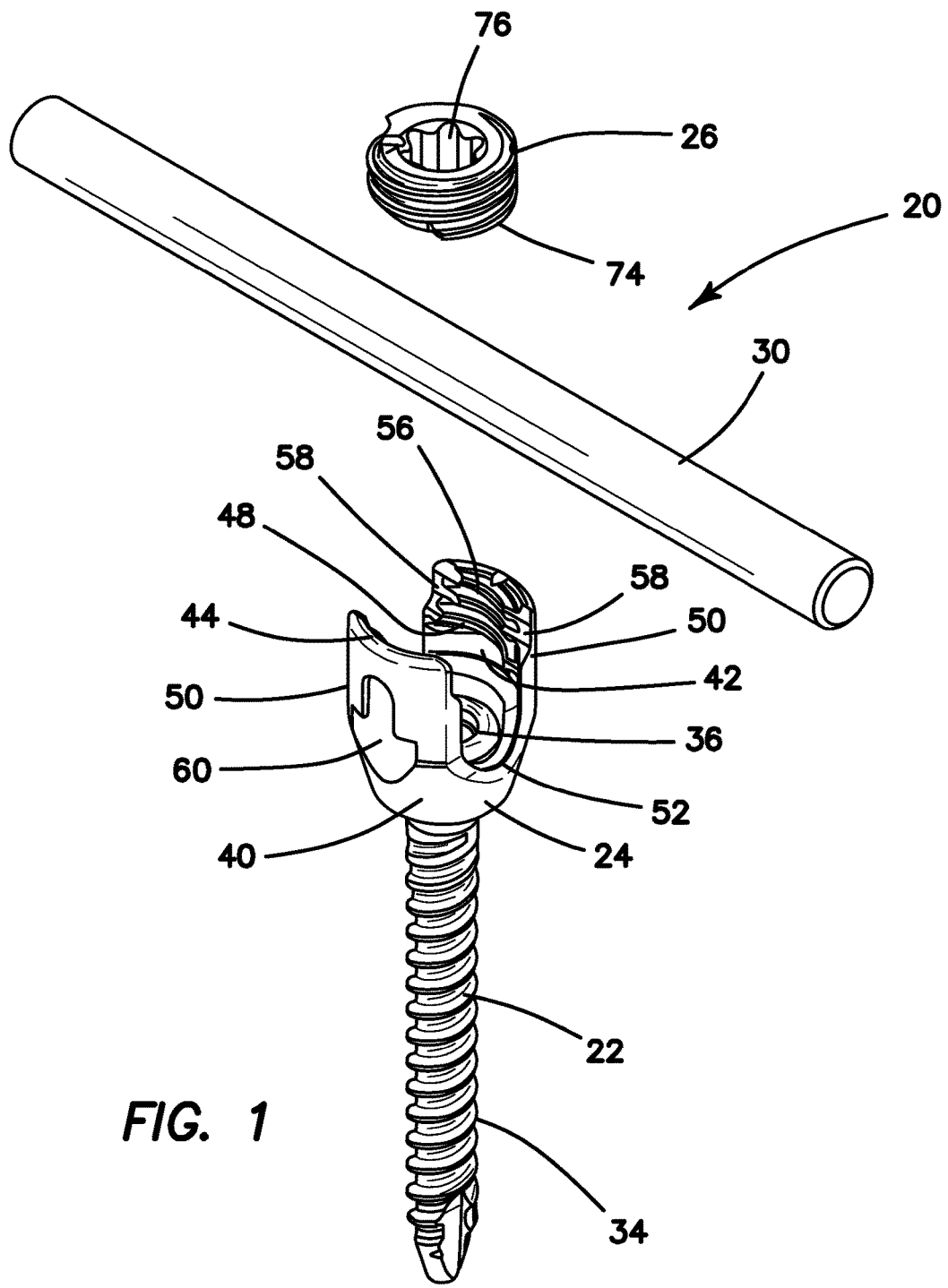
FIG. 1 is a top perspective, exploded view of a bone fixation system and connecting rod according to the present invention.
Figure 2:
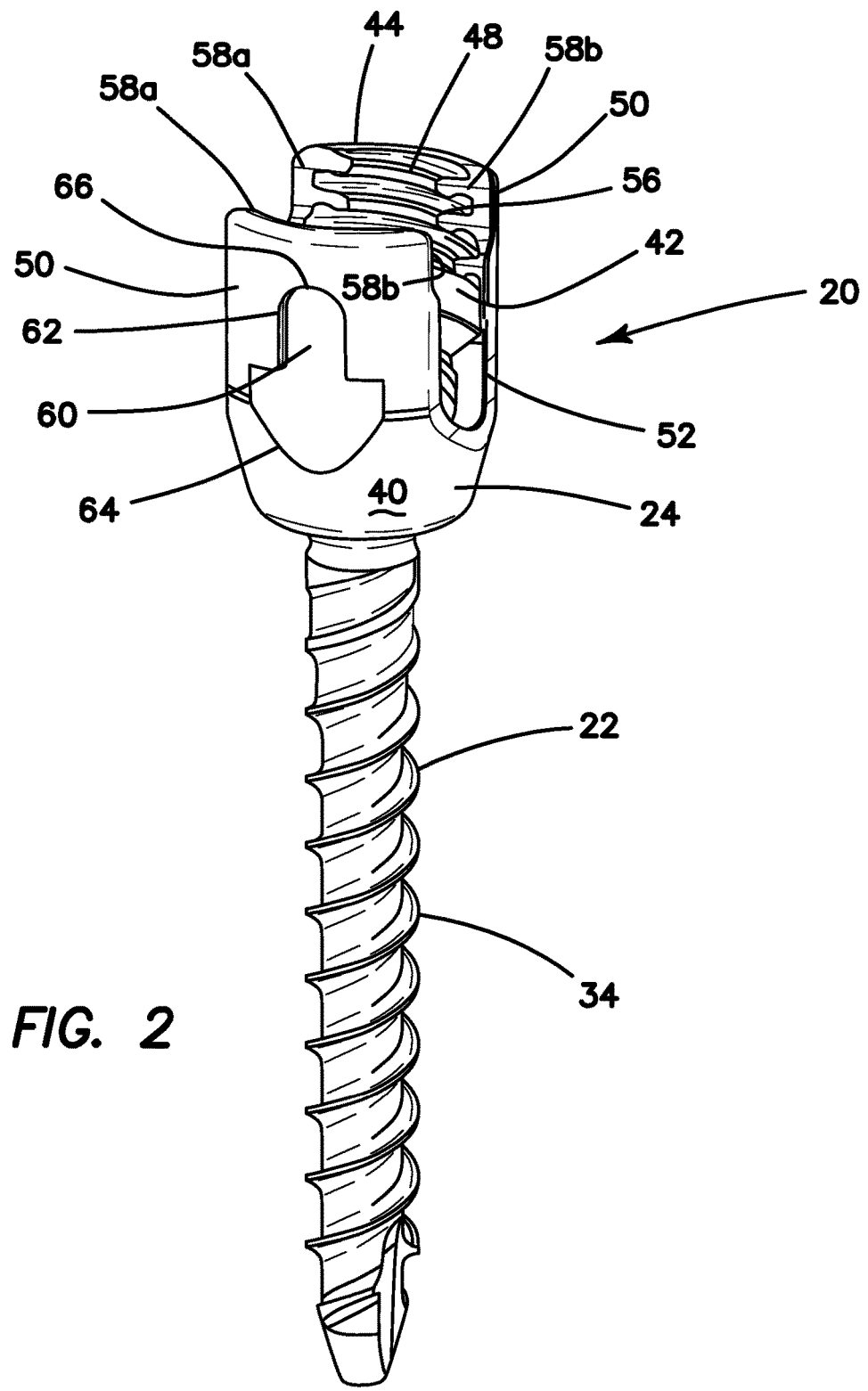
FIG. 2 is a top perspective view of a bone fastener and receiver according to the present invention.
Figure 3:
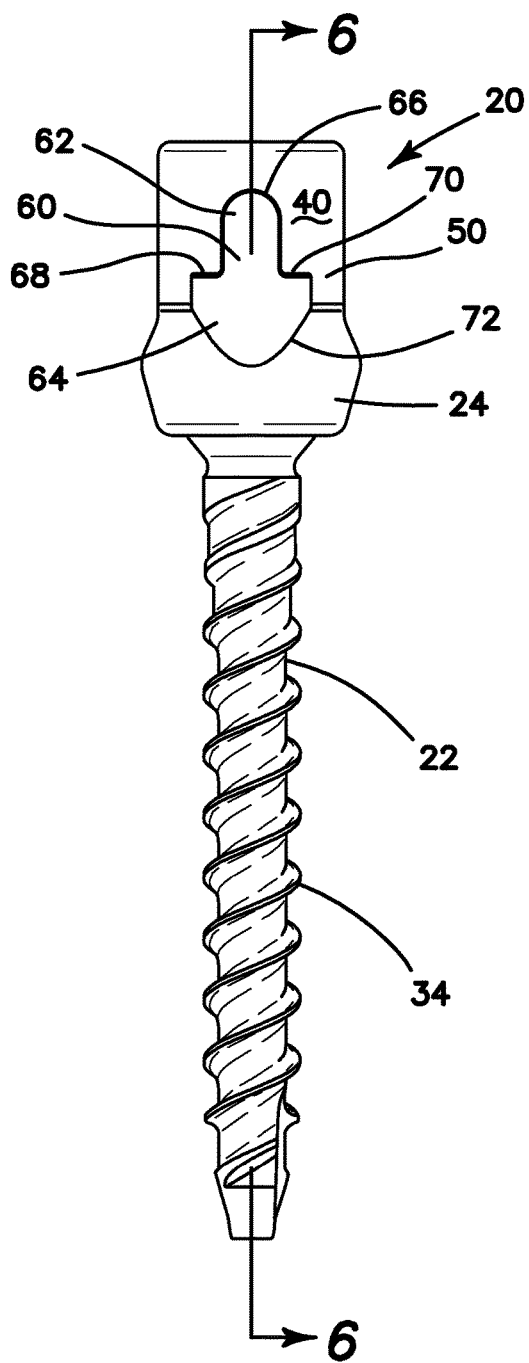
FIG. 3 is a side elevational view of a bone fastener and receiver according to the present invention.
Figure 4:
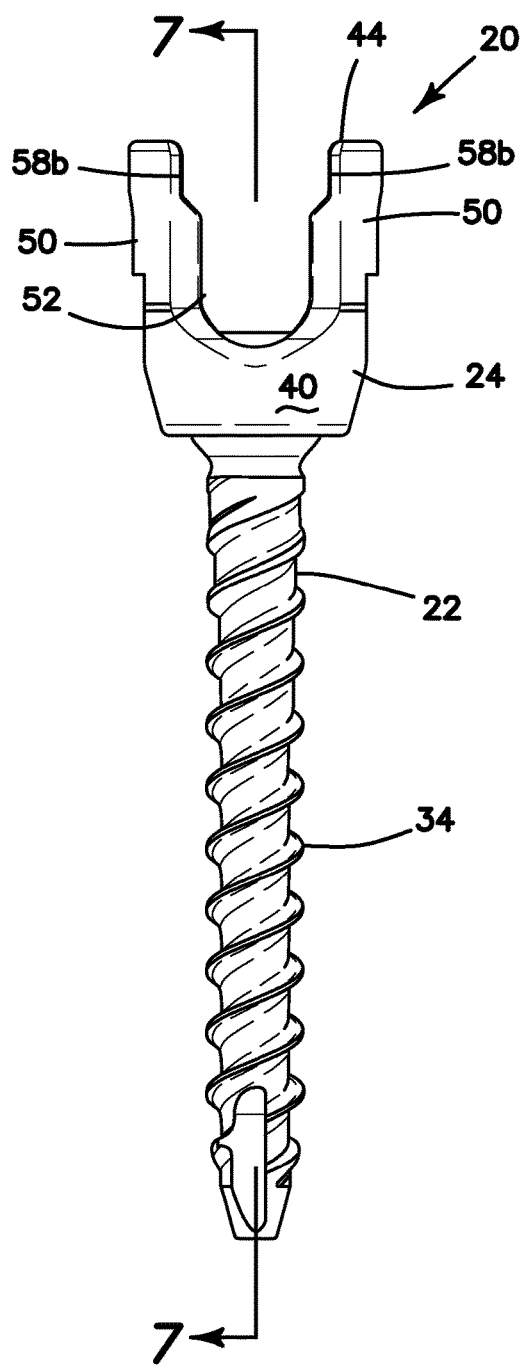
FIG. 4 is a side elevational view of a bone fastener and receiver according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It should also be understood that the term "system", when referring to a system of the present invention, may refer to a set of components which includes multiple bone stabilization components such as a superior or cephalad component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween. The term "system" may also include an insertion instrument and/or stabilization rod or element.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intra-operatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means or fixation devices such as elongate fixation members, rods and plates but are not limited thereto. In other embodiments, components interface, in a manner that constrains their relative movement and enables the treated segment to mimic the function or partial function and/or movement or partial movement of a healthy segment. Typically, spinal interconnecting means is a dorsally positioned component, i.e., positioned posterior of the superior and inferior components, or may be a laterally positioned component, i.e., positioned to the outer side of the posterior and inferior components. The structures may include one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts. In addition, each of the inventive embodiments described herein may be employed in a percutaneous, minimally invasive surgical procedure, a mini-open procedure or an open procedure. Utilization of minimally invasive techniques can shorten the procedure's time and speed recovery by the patient. The application of these inventions in a minimally invasive manner is not a requirement. Also, the invention is not limited to the spine and may be employed in other areas where fixation to bone is useful either in human or animal applications.

Turning to FIGS. 1-7, there is shown a bone fixation system 20 suitable for use in orthopedic surgery. In particular, the bone fixation system 20 of the present invention is adapted for use in spinal fixation procedures and as such can be installed in a patient for treating at least one or more of the following: degenerative disc disease, spinal stenosis, spondylolisthesis, spinal deformities, fractures, pseudarthrosis, tumors, failed previous fusions, other vertebral segment trauma or diseases. However, the invention is not so limited and various aspects of the present invention may have application for other procedures. The bone fixation system 20 includes a bone fastener 22, a receiver also called a tulip 24 coupled to the bone fastener 22, and a rod locking cap also called a set screw 26. The bone fixation system 20 may also include an insertion instrument 28 configured to implant the bone fastener 22 into bone. Also, the bone fixation system 20 may include an elongate fixation member also called a connecting rod 30. It should be noted, however, that although the bone fixation system 20 is generally illustrated and described as a single assembly for use with a single connecting rod 30, any combination of bone fixation systems 20 and connecting rods 30 can be employed during a surgical procedure. For example, in a single level spinal fixation procedure, two bone fixation systems 20 can receive a single connecting rod 30 along one side of the spine and two bone fixation systems 20 can receive another connecting rod 30 along the opposite side of the spine. A multiple level spinal fixation procedure, however, will generally require additional bone fixation systems 20. In addition, the bone fixation systems 20 need not be coupled to adjacent vertebral bodies, but rather, the bone fixation systems 20 can be positioned so as to skip adjacent vertebral bodies if desired. The bone fixation system 20 can be composed of any suitable material, such as titanium, stainless steel, metal, metal alloys, polymers, synthetic polymers such as polyether ether ketone (PEEK), plastics or any other sufficiently rigid and strong material which is biologically compatible and can maintain its strength in vivo for at least six months. The various components of the bone fixation system 20 can be made of materials that are different from the other components of the system 20.

Figure 5:
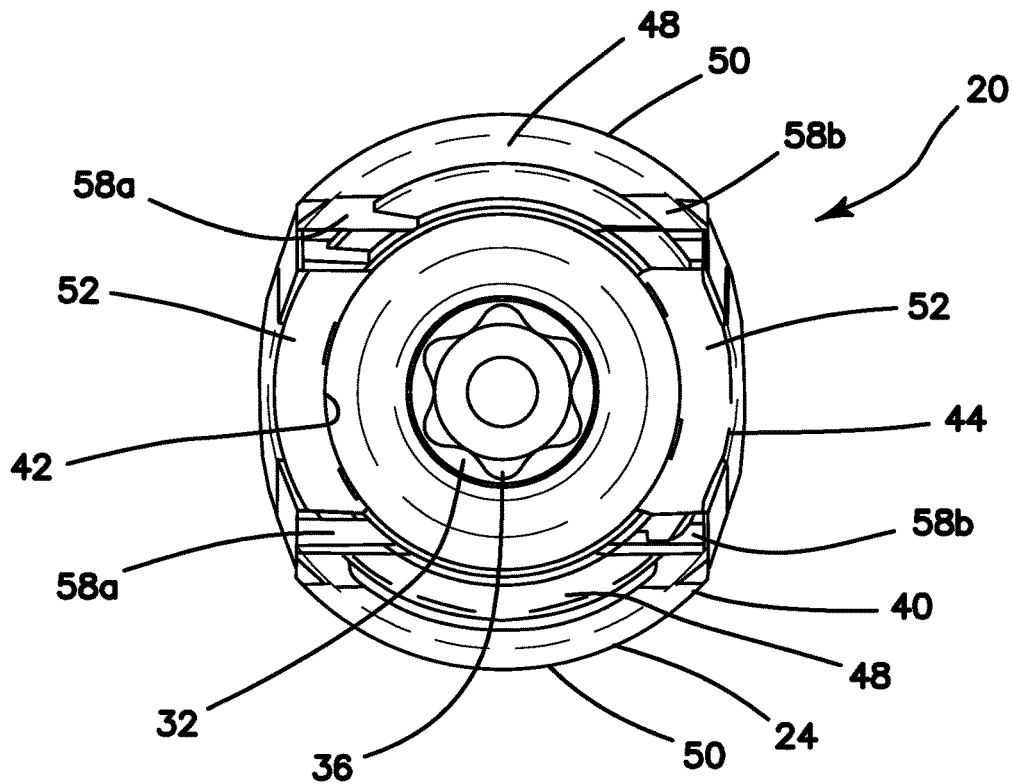
FIG. 5 is a top view of a bone fastener and receiver according to the present invention.

Still referencing FIGS. 1-7, the bone fastener 22 is configured to engage the anatomy to couple the bone fixation system 20 to the anatomy. The bone fastener 22 includes a head 32 at a proximal end and an elongate threaded shank portion 34 extending between the head 32 and a distal end along a longitudinal axis. The bone fastener 22 is configured as a typical bone screw; however, the invention is not so limited and any fastener or other-shaped anchor may be employed such as a laminar hook. The bone fastener 22 may be a self-tapping bone screw having at least one cutting flute. Alternatively, a bone screw that requires a hole to be pre-tapped prior to insertion may be employed. The head 32 can be generally arcuate having a curved or bulbous outer surface and may be spherical, frusto-spherical or partially spherical in shape. The head 32 can include a driver connection socket 36 at the proximal end visible in FIG. 5 for mating with any type of driver such as a hex tool having a hexagonal distal tip to enable the application of torque to drive the bone fastener 22 into the anatomy. A daisy-shaped driver connection socket 36 is shown in FIG. 5. Generally, the head 34 has a wider lateral dimension relative to the lateral dimension of the shank portion 34.

Still referencing FIGS. 1-7, the tulip or receiver 24 will now be described in detail. The receiver 24 includes a sidewall 38 having an outer surface 40 and an inner surface 42. The sidewall 38 forms a proximal opening 44 at the proximal end leading into a substantially cylindrical inner bore that extends to a distal opening 46 at the distal end of the receiver 24. The distal opening 46 is configured for receiving at least a part of the shank portion 34 and/or head 32 of the bone fastener 22. The inner surface 42 of the receiver 24 at the distal end receives the bone fastener 22. The inner surface 42 of the receiver 24 at the distal end is contoured to form a conforming seat for the bone fastener 22 such that when the bone fastener 22 is inserted into the distal opening 46, the bone fastener 22 may freely pivot and angulate polyaxially unimpeded relative to the receiver 24 as well as rotate about the longitudinal axis of the bone fastener 22.

The sidewall 38 of the receiver 24 forms two upstanding, oppositely disposed arms 50. The arms 50 are spaced apart from each other to define at least one channel 52 in the sidewall 38. In one variation, the channels 52 comprise two oppositely disposed, substantially U-shaped spaces that interconnect with the proximal opening 44 and the inner bore of the receiver 24. The channels 52 are shaped to receive an elongate fixation member 30 such as a spinal fixation rod or other elongate member to be connected to the receiver 24 by placement of the elongate fixation member 30 into the one or more channel 52. The channels 52 seat an elongate fixation member 30 above the bone fastener 22. The inner surface 42 of the two upstanding arms 50 includes threads 48 or inner interlocking surfaces. The oppositely disposed threaded portions 56 extend longitudinally vertically on the arms 50 and are configured to threadingly engage threads or other complimentary interlocking features formed on the outer surface of the set screw 26. The threads 48 on the inner surface 42 define a major inner diameter measured from root-to-root of the threads 48 between the arms 50 and a minor inner diameter measured from crest-to-crest of the threads 48 between the arms 50.

Adjacent to the threaded portions 56 on each arm 50 are two oppositely disposed flats also called smooth surfaces 58. A first smooth surface 58a and a second smooth surface 58b extend longitudinally vertically along the arm 50 from the edge of the outer surface 40 into the threads 48. Each smooth surface 58 commences at the outer surface 40 of the arm 50 and extends inwardly to the inner surface 42. In another variation, the first smooth surface 58a and the second smooth surface 58b of one arm 50 are parallel to each other and extend contiguously with a chord that is parallel to the outer diameter or inner diameter of the receiver 24. The first smooth surface 58a and the second smooth surface 58b of the opposite arm 50 are also parallel to each other and extend contiguously with a chord that is parallel to the outer diameter or inner diameter of the receiver 24 such that all of the smooth surfaces 58 are parallel to each other and form parallel surface segments or opposed pairs of chordal surfaces in which the first smooth surface 58a on one arm 50 is parallel and opposite to the first smooth surface 58a on the opposite arm 50 and the second smooth surface 58b on one arm 50 is parallel and opposite to the second smooth surface 58b on the opposite arm 50. In another variation, the first smooth surface 58a is angled with respect to the second smooth surface 58b on the same arm 50. Each smooth surface 58 extends through the threads 48 from major diameter to the minor diameter of the threads 48. Therefore, the intersection of the each smooth surface 58 with the inner surface 42 is irregular in shape.

The outer surface 40 of the receiver 24 includes two recesses 60 oppositely disposed in the arms 50 for permitting an insertion instrument 28 or other instrument to grasp onto the receiver 24, attach to the receiver 24 for the purposes of implanting or extracting the bone fixation system 20, threading the bone fastener 22 into bone, inserting a connecting rod 30, moving a connecting rod 30 within the channels 52 to seat the connecting rod 30, and attaching the set screw 26. Each recess 60 substantially conforms in shape and size to a prong extension of an instrument 28. Each recess 60 extends radially inwardly from the outer surface 40 to define a recessed surface having perimeter a perimeter surface comprising a plurality of distinct intersecting surfaces. In one variation, the recess 60 is arrow-shaped having a narrow central portion 62 and a wider portion 64 relative to the central portion 62 that forms an arrow-like shape that points downwardly. The central portion 62 includes a first proximal surface 66 that extends laterally to the longitudinal axis of the receiver 24. The central portion 62 includes two side surfaces that interconnect with the wider portion 64. The wider portion 64 includes a second proximal surface 68 and a third proximal surface 70. The second proximal surface 68 and the third proximal surface 70 are located on either side of the central portion 62 and each extends laterally to the longitudinal axis of the receiver 24. The second proximal surface 68 is interconnected to the third proximal surface 70 by a distal surface 72 of the recess 60. Hence, the recess 60 is defined by the first proximal surface 66, side surfaces, the second and third proximal surfaces 68, 70 and the distal surface 72. This variation of the recess 60 includes three lateral surfaces that are separate by two intervening surfaces which in this variation are formed by the side surfaces of the central portion 62. The lateral surfaces 66, 68 and 70 each have a component that is perpendicular or lateral to the longitudinal axis of the receiver 24 or extend along the outer surface having a circumferential component or surface perpendicular to the longitudinal axis of the receiver. The recesses 60 on each arm 50 and their advantageous interconnection with an instrument 28 will be described in greater detail below.

With reference back to FIG. 1, the rod locking cap or set screw 26 will now be described in greater detail. The set screw 26 is a substantially cylindrical object having an outer surface interconnected with a top surface and a bottom surface. The outer surface includes threads 74 and is configured to fit inside the receiver 24 and threadingly engage with the threads 48 on the inner surface 42 of the arms 50 of the receiver 24. The top surface of the set screw 26 includes a driver-receiving connection bore or socket 76 configured for engaging the tip of a driving instrument for turning the set screw 26 between a locked position and an unlocked position. The bottom surface of the set screw 26 may include a conforming surface that conforms to the outer contour of a connecting rod 30. As the set screw 26 is threadingly translated downwardly into threaded engagement with the inner bore of the receiver 24 via threads 48, it will bear down with force onto the connecting rod 30 to lock it into the desired position and further downward threaded engagement will result in the connecting rod 30 bearing down with force onto the head 32 of the bone fastener 22 locking its angulation in place. It is understood that threads may be substituted for any mechanical interlocking surface feature where suitable and appropriate.

With continued reference to FIG. 1, the elongate fixation member 30 is a typical spinal fixation rod having a solid cylindrical shape having a circular cross-section and a length that spans any number of vertebrae that are desired to be fixed. A short portion of the elongate fixation member 30 is pictured in the figures for exemplary purposes only. Although a spinal fixation rod 30 is pictured, the use of any fixation member having any cross-section is within the scope of the present invention.

The bone fixation system 20 is assembled by passing the shank portion 34 of the bone fastener 22 through the proximal opening 44 and into the distal opening 46 in the receiver 24 with the head 32 coming to rest in the seat of the receiver 24. An additional retainer (not shown) may be employed if the distal opening 46 is too large to retain the head 32 of the bone fastener 22. The retainer forms an additional seating location for the bone fastener 22 permitting it to be retained inside the receiver 24. A retaining ring 78 may also be used and located above the head 32 of the bone fastener 22 to keep the bone fastener 22 connected to the receiver 24. The retaining ring 78 may also provide a seating surface for the connecting rod 30 as well as serve to transfer force to the bone fastener 22 to lock the bone fastener 22 against the receiver 24, thereby, also locking its angulation with respect to the receiver 24. A connecting rod 30 is located between the arms 50 within the channel 52 of the receiver 24. The connecting rod 30 is permitted to slide inside the channel 52 and when the desired position is ascertained, the set screw 26 which is inserted between the arms 50 into the receiver 24 is threadingly engaged downwardly to lock the translation of the connecting rod 30 relative to the receiver 24. Continued downward threaded engagement of the set screw 26 results in the set screw 26 bearing down upon the connecting rod 30 locking it into position and further tightening will bear down onto the retaining ring 78 and push the bone fastener 22 against the receiver 24 locking its angulation relative to the receiver 24. Prior to insertion of a connecting rod 30, a driver is inserted into the inner bore of the receiver 24 and through an aperture of a retaining ring 78 if one is used to engage the driver connection feature 36 in the head 32 of the bone fastener 22. The driver is then turned to drive the bone fastener 22 into the bone anatomy. With the shank portion 34 resident in the anatomy, the receiver 24 is permitted to angulate relative to the bone fastener 22 until the set screw 26 is threaded to a locked position. The set screw 26 may be rotated in an opposite direction to unlock the connecting rod 30 and also unlock the receiver 24 relative to the bone fastener 22 so that the angulation of the receiver 24 may be adjusted and relocked as desired. This may be repeated as needed.

Figure 8:
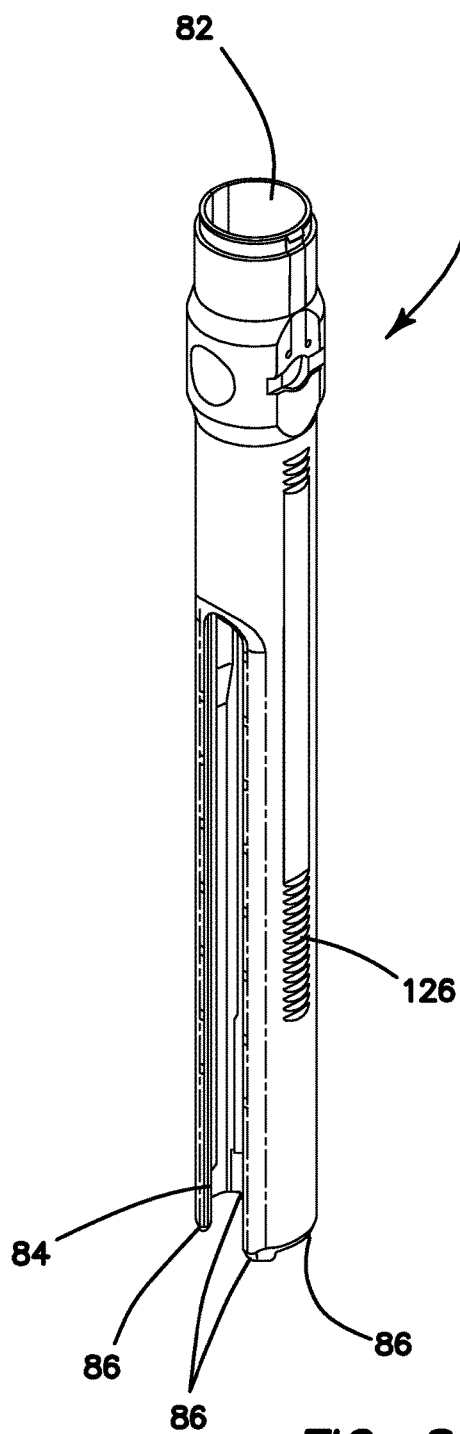
FIG. 8 is a top perspective view of an instrument tower according to the present invention.

Turning now to FIGS. 8-11, the assembly of an instrument 28 used for inserting and extracting the bone fixation system 20 will now be described. With particular reference to FIG. 8, a tower 80 is shown. The tower 80 is elongated and includes a central lumen 82 extending from an open proximal end to an open distal end. The distal end of the tower 82 includes two oppositely disposed slots 84 extending proximally from the opening at the distal end. The distal end of the tower 80 includes four hooks 86. Each hook 86 is formed on the tower 80 at the four intersections of the tower 86 and the two slots 84. These hooks 86 will be described in greater detail below.

Figure 9:
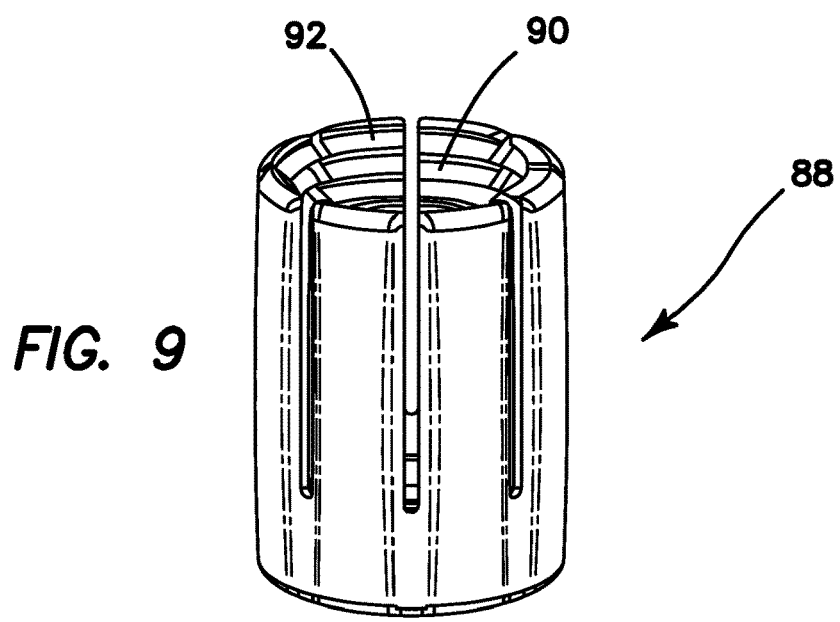
FIG. 9 is a top perspective view of an instrument knob according to the present invention.
Figure 6:
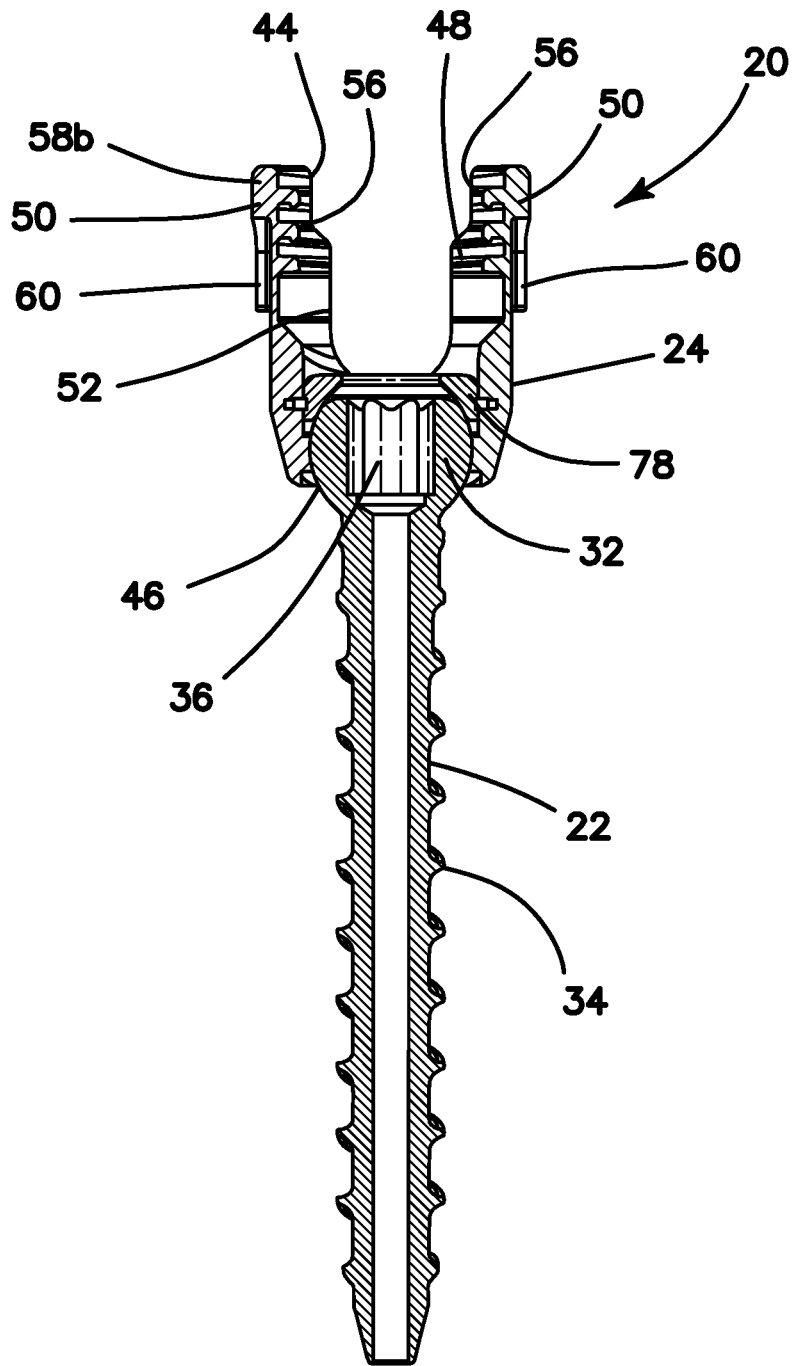
FIG. 6 is a cross-sectional view taken along line 6-6 of FIG. 3 of a bone fastener and receiver according to the present invention.
Figure 7:
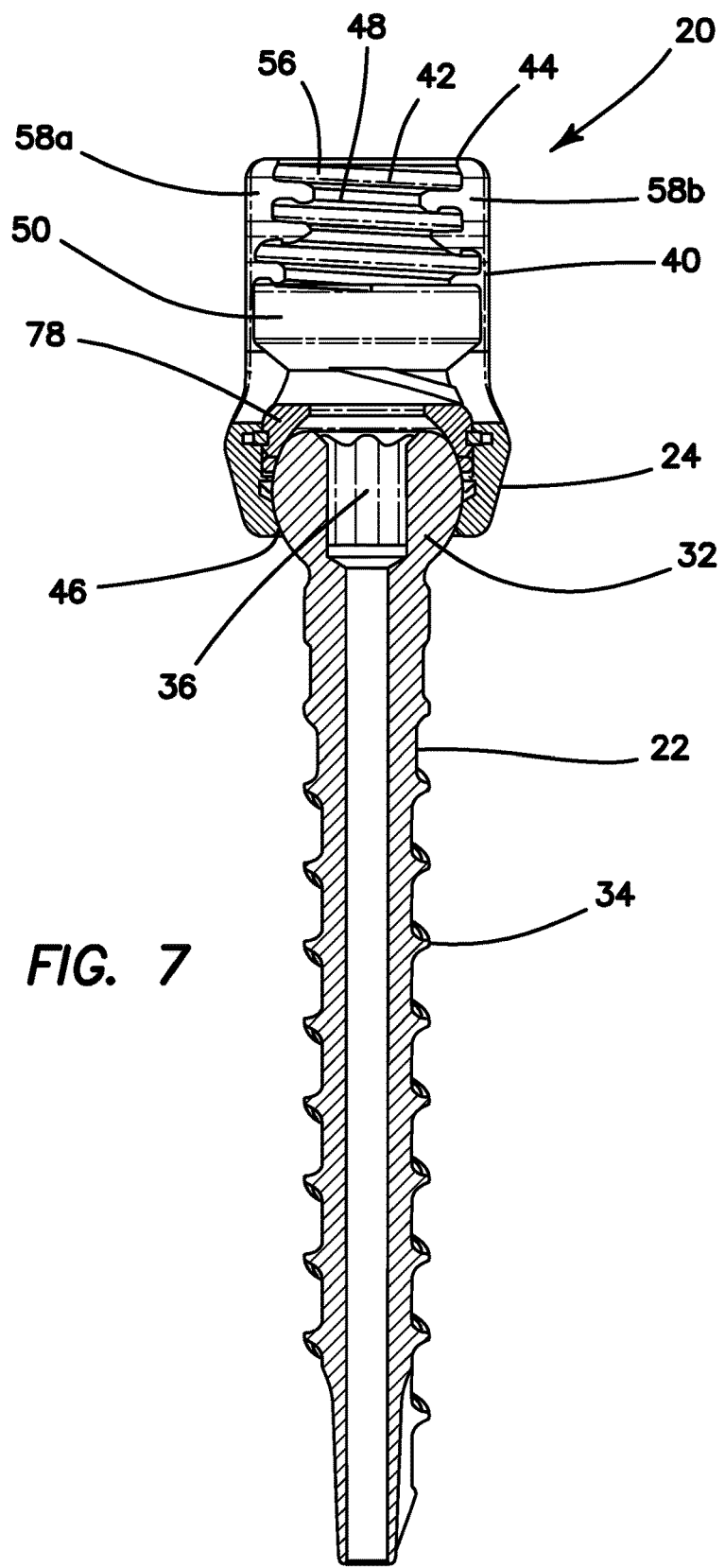
FIG. 7 is a cross-sectional view taken along line 7-7 of FIG. 4 of a bone fastener and receiver according to the present invention.

Turning now to FIG. 9, there is shown a knob 88 having a cylindrical shape with a central lumen 90 and an inner surface with threads 92. The knob 88 is connected to the proximal end of the tower 80 such that the knob 88 may freely rotate with respect to the tower 80.

Figure 10:
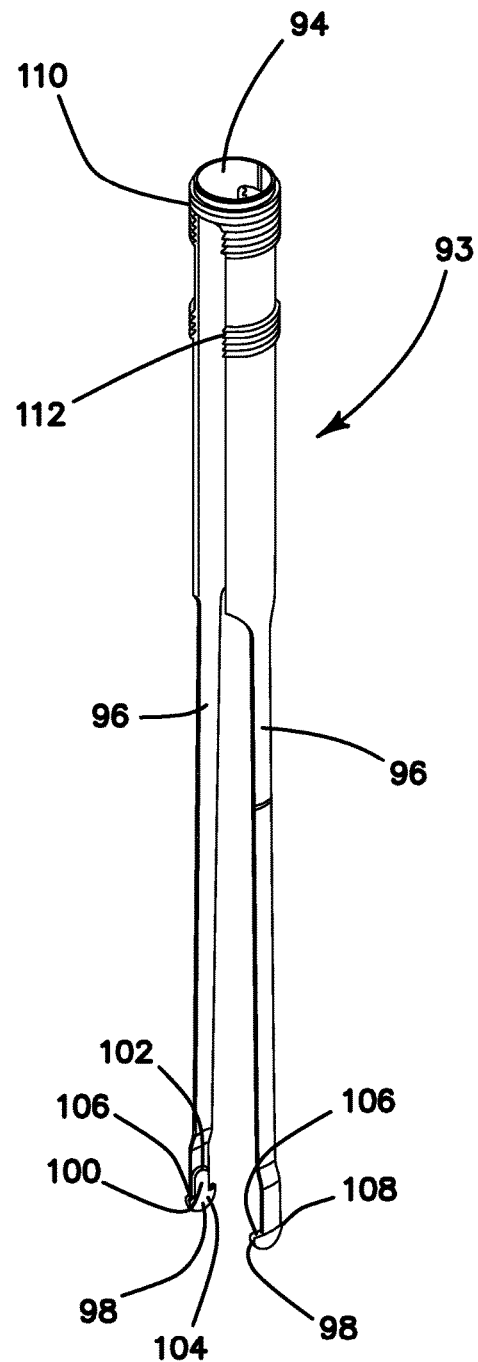
FIG. 10 is a top perspective view of an instrument inner shaft according to the present invention.

FIG. 10 illustrates an inner shaft 93. The inner shaft 93 has a substantially cylindrical shape that defines a central lumen 94. The inner shaft 93 includes two oppositely disposed prongs 96 that extend distally to their free ends. Each prong 96 includes an inner surface and an outer surface. The distal end of each prong 96 is configured for connecting to the receiver 24 and, as such, the prongs 96 are capable of flexing inwardly and outwardly with respect to the proximal end of the inner shaft 93. In one variation, the prongs 96 are biased outwardly in an open configuration. The inner surface of the distal end of the prong 92 is bowed or angled slightly outwardly relative to the greater length or mid-section of the prong 92. At the distal end, the inner surface of each prong 92 includes an inwardly extending protrusion or prong extension 98 that has a shape that conforms to the recess 60 on the receiver 24 to which the prong 92 is configured to connect. The extension 98 is a male member configured to connect with the female member recess 60 on the receiver 24. In one variation, the prong extension 98 includes a central portion 100 having a width and defining a first proximal surface 102. The central portion 100 is interconnected with a distal wider portion 104 having a second proximal surface 106 and a third proximal surface 108 located on either side of the central portion 100. The shape of the prong extension 98 corresponds and conforms to the shape of the recess 60 on the receiver 24. The proximal end of the inner shaft 93 includes a first threaded section 110 that is spaced apart from and proximal to a second threaded section 112. The inner shaft 93 is sized and configured to be inserted into the central lumen 82 of the tower 80. The prongs 96 are inserted in through the proximal opening of the tower 80 until the second threaded section 112 of the inner shaft 93 contacts the inner threads 92 of the knob 88. The second threaded section 112 is threaded with the inner threads 92 of the knob 88 until the second threaded section 112 is located distally to the inner threads 92. As a result, the inner shaft 93 is connected to the tower 80 such that the tower 80 can translate back-and-forth relative to the inner shaft 93 between the first threaded section 110 and the second threaded section 112.

Figure 11:
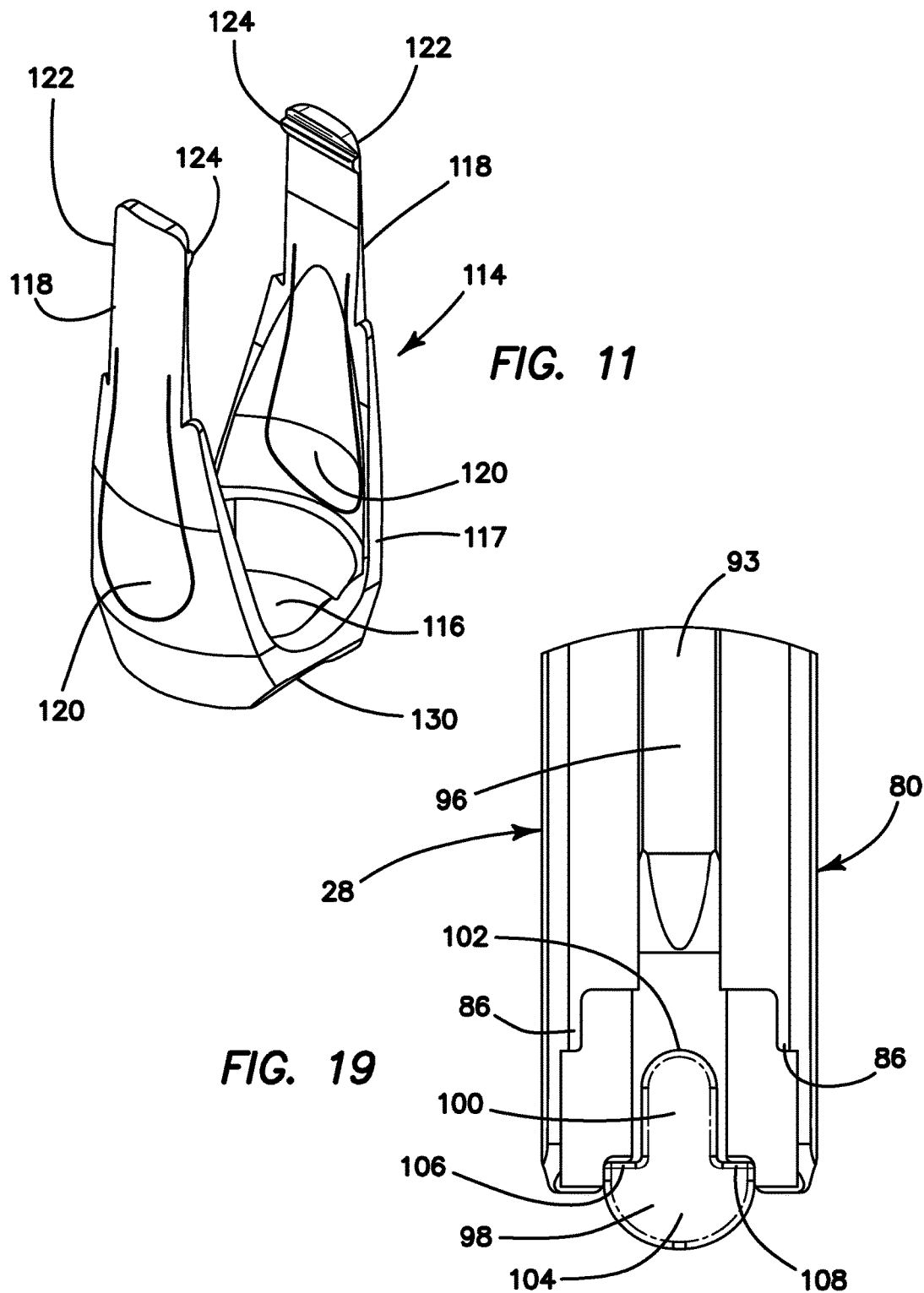
FIG. 11 is a top perspective view of an instrument reducer according to the present invention.

As shown in FIG. 11, the instrument 28 may further include a reducer 114. The reducer 114 includes is substantially cylindrical in shape and includes a central opening 116. The reducer 114 includes main body 117 and two fingers 118 that are cantilevered with respect to the main body 117 such that the fingers 118 can flex outwardly. In particular, the fingers 118 are connected to the main body 117 near the center of each finger 118 such that by pressing distal finger locations 120 inwardly toward the longitudinal axis, the proximal ends 122 of the fingers118 will move outwardly away from the longitudinal axis. The inner surface of each of the fingers 118 at their proximal ends includes at least one tooth 124 that extends inwardly toward the longitudinal axis of the reducer 114. Each tooth 124 is configured to engage and releasably lock with a rack 126 on the tower 80 shown in FIG. 8. The tower 80 includes two oppositely disposed racks 126 each having a plurality of teeth configured to engage with a tooth 124 on the reducer 114. The reducer 114 is connected to the tower 80 by inserting the distal end of the tower 80 into the central opening 116 in the reducer 114 and sliding the reducer 114 over the tower 80 including sliding the reducer 114 over the rack 126 on the tower 80 to a position proximal to the rack 126. A second rack 128 of teeth may be provided on the outer surface of the tower 80 at a location proximal to the first rack 126. The second rack 128 permits engagement with the teeth 124 on the reducer 114 to hold the reducer 114 fixed in position relative to the tower 80. The reducer 114 is configured such that it will easily slide in the distal direction relative to the tower 80 with the teeth 124 ramping over the proximal faces of the teeth in the first and second racks 126, 128. The proximal movement of the reducer 114 is resisted by the configuration of teeth in the first and second racks 126, 128 locking the reducer 114 in position relative to the tower 80. The reducer 114 may be released from being locked to the first rack 126 or second rack 128 by depressing the distal finger locations 120 on the fingers 118 to flex the proximal ends 122 of the fingers 118 and their teeth 124 out of engagement with their respective racks 126, 128 so that the reducer 114 may slide proximally with ease. As such, the reducer 114 is advantageously configured to slide distally easily and relatively unimpededly and remain locked from proximal movement. The distal end of the reducer 114 may be curved or include surface 130 that conforms to the shape of the connecting rod 30 resident inside a channel 52 to be reduced or pushed in the distal direction relative to the instrument 28. Sometimes great force is required to reduce or push a connecting rod 30 located inside the channel 50 in a distal direction relative to the instrument 28 in order to seat the connecting rod 30 deeply inside the channel 50 so that a set screw 26 may be inserted and tightened to attach the connecting rod 20 firmly to the bone fixation system 20. The reducer 114 reduces the distance between the connecting rod 20 and the receiver 24. The unidirectional locking feature of the reducer 114 relative to the tower 80 permits the reducer 114 to be moved incrementally in the distal direction tooth-by-tooth along the first rack 126 with corresponding tooth-by-tooth locking of the reducer 114 and, hence, connecting rod 30 in place. If it is desired to reposition the connecting rod 30 relative to the instrument 28, the distal finger locations 120 on the reducer 114 fingers 118 are simply depressed to release the teeth 124 and unlock the reducer 114 freeing it for proximal movement and, thereby, allowing the connecting rod 30 to be repositioned proximally.

Turning now to FIGS. 12-15, there is shown the instrument 28 in an unlocked or open configuration. The instrument 28 includes an unlocked configuration in which the tower 80 is positioned proximally along the inner shaft 93 such that the prongs 96 are exposed in an open, wide angle, splayed-out configuration. In the open unlocked configuration the prongs 96 are capable of being flexed inwardly by movement of the tower 80 over the prongs 96. In the unlocked configuration, the inner threads 92 of the knob 88 are located near the first threaded section 110. In such a location, the tower 80 can easily slide distally relative to the inner shaft 93 to a locked configuration in which the prongs 96 are flexed inwardly and covered by the tower 80. The inner shaft 93 may be locked in the unlocked configuration by threading the inner threads 92 of the knob 88 and the first threaded section 110 together. While in the unlocked configuration, the instrument 28 may be placed into a position such that the prongs 96 are outside of the receiver 24 and in juxtaposition with the recesses 60 ready to engage the prong extensions 98 into the recesses 60 on the receiver 24. When moved from an unlocked configuration to a locked configuration, the tower 80 is moved distally relative to the inner shaft 93 and over the bowed-out prongs 96 flexing the prongs 96 inwardly towards each other and into their respective recesses 60 to attach the bone fixation system 20 to the instrument 28.

Figures 12, 16, 22:
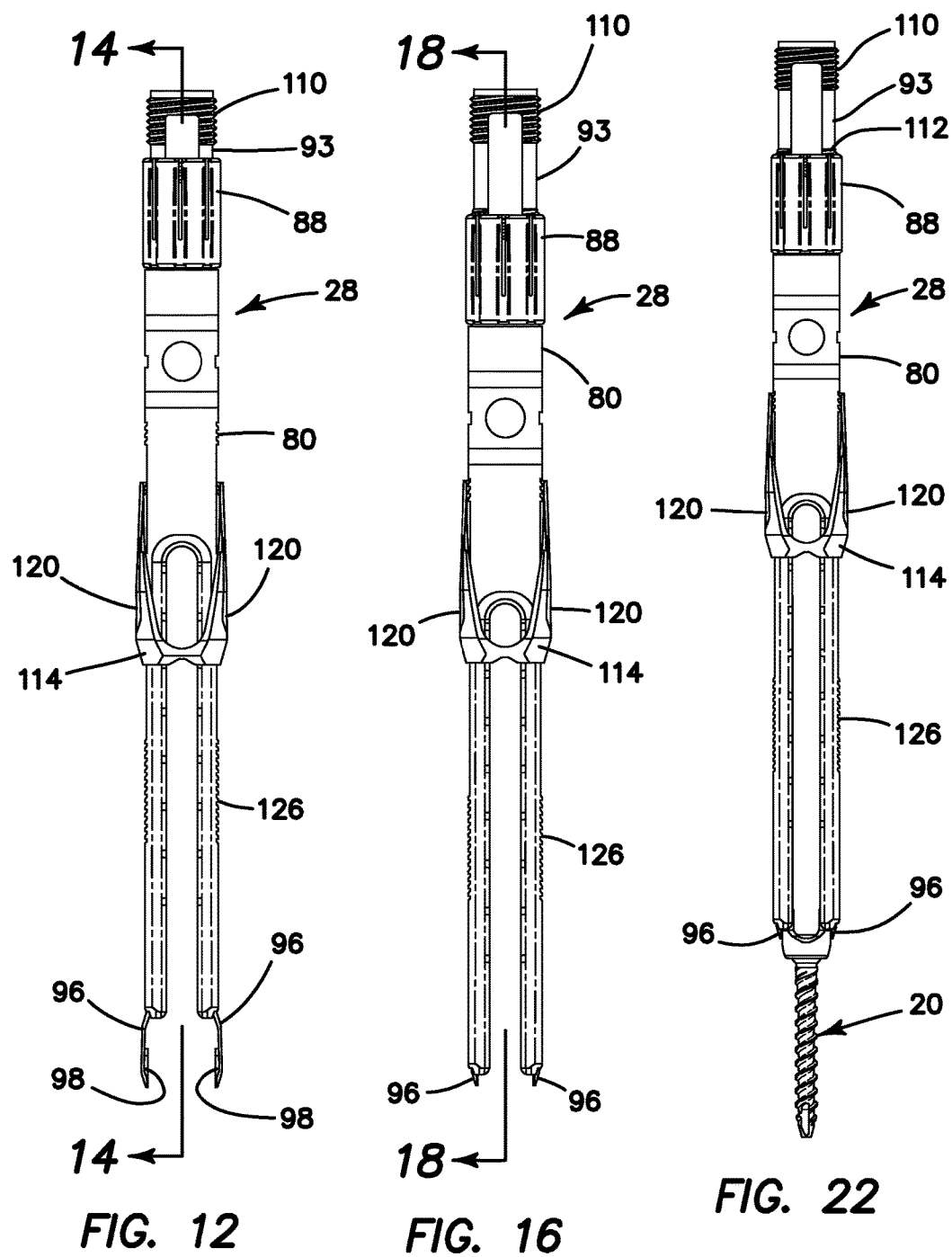
FIG. 12 is a side elevational view of an instrument in an open configuration according to the present invention.
FIG. 16 is a side elevational view of an instrument in a closed configuration according to the present invention.
FIG. 22 is a side elevational view of a bone fixation system and instrument in a closed configuration according to the present invention.
Figure 13:
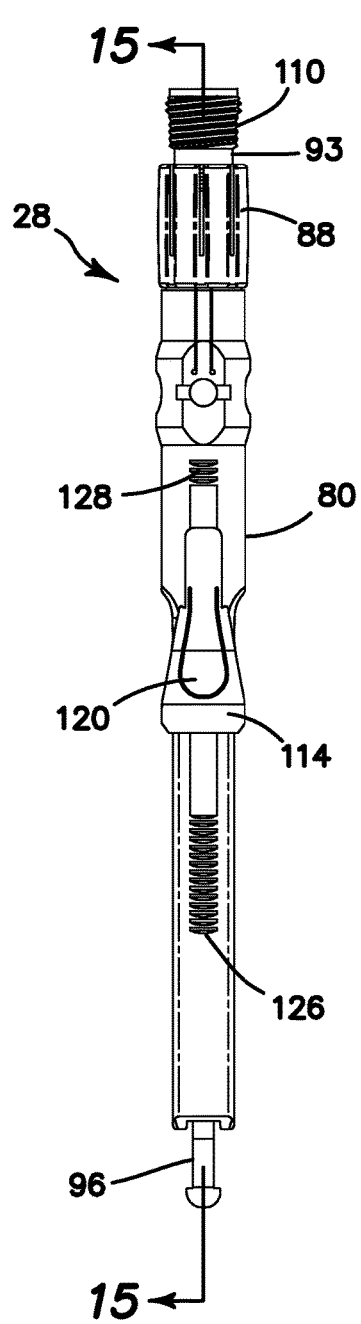
FIG. 13 is a side elevational view of an instrument in an open configuration according to the present invention.
Figure 17:
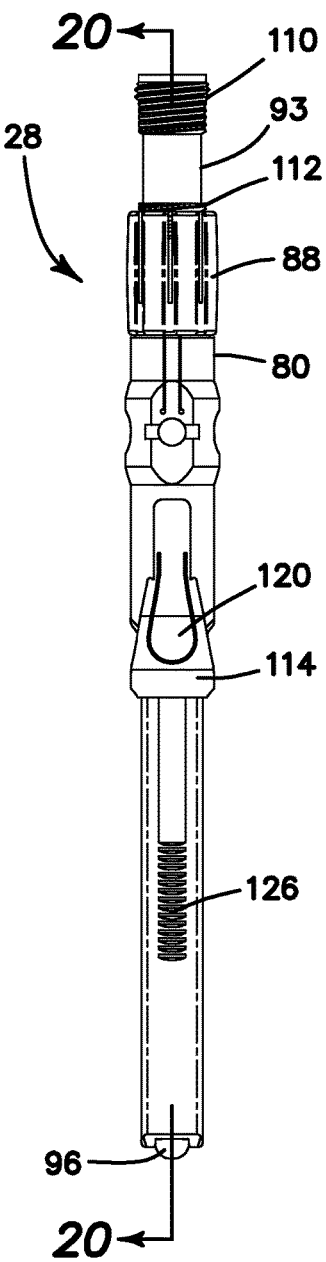
FIG. 17 is a side elevational view of an instrument in a closed configuration according to the present invention.
Figure 23:
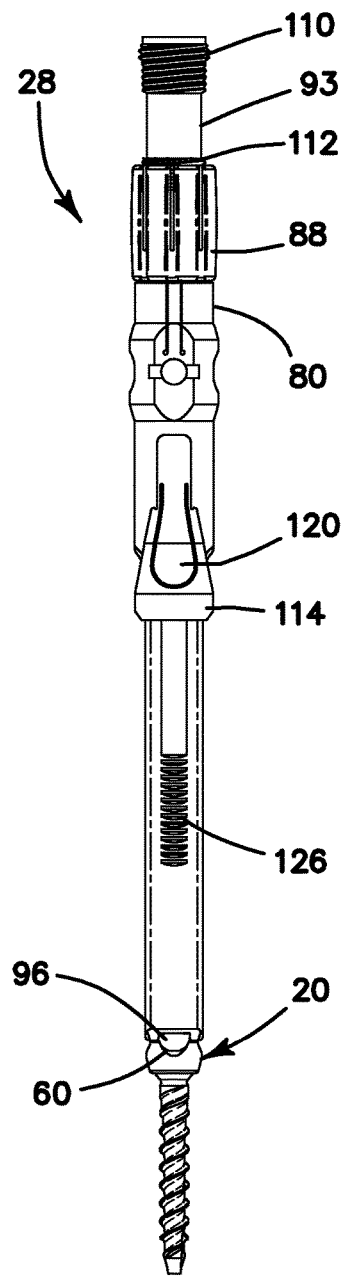
FIG. 23 is a side elevational view of a bone fixation system and instrument in a closed configuration according to the present invention.
Figure 14:
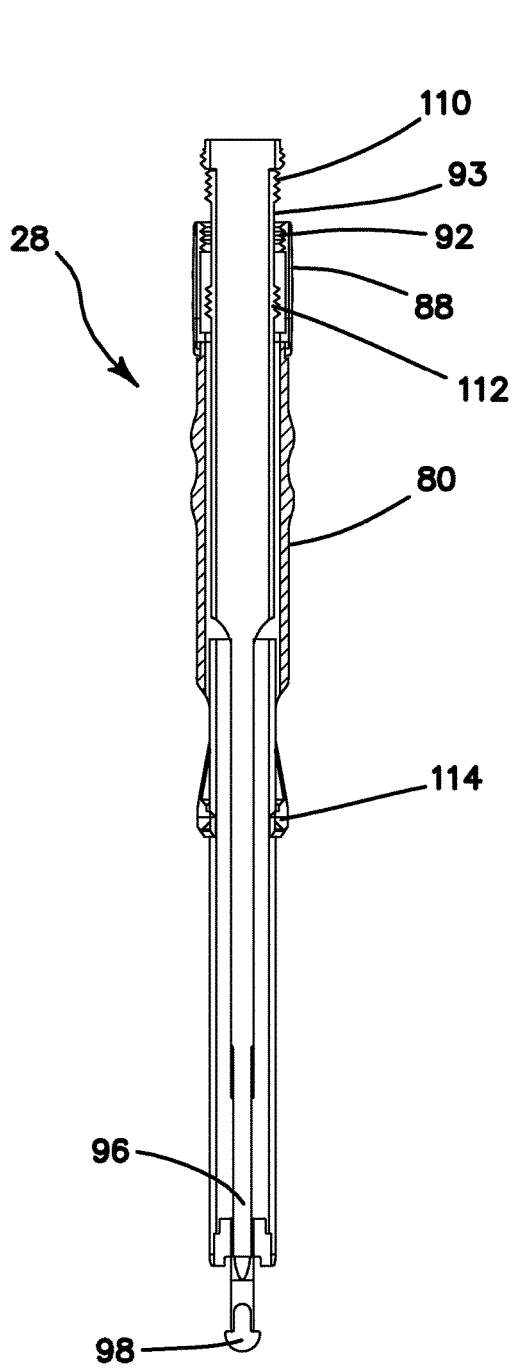
FIG. 14 is a cross-sectional view taken along line 14-14 of FIG. 12 of an instrument in an open configuration according to the present invention.
Figure 18:
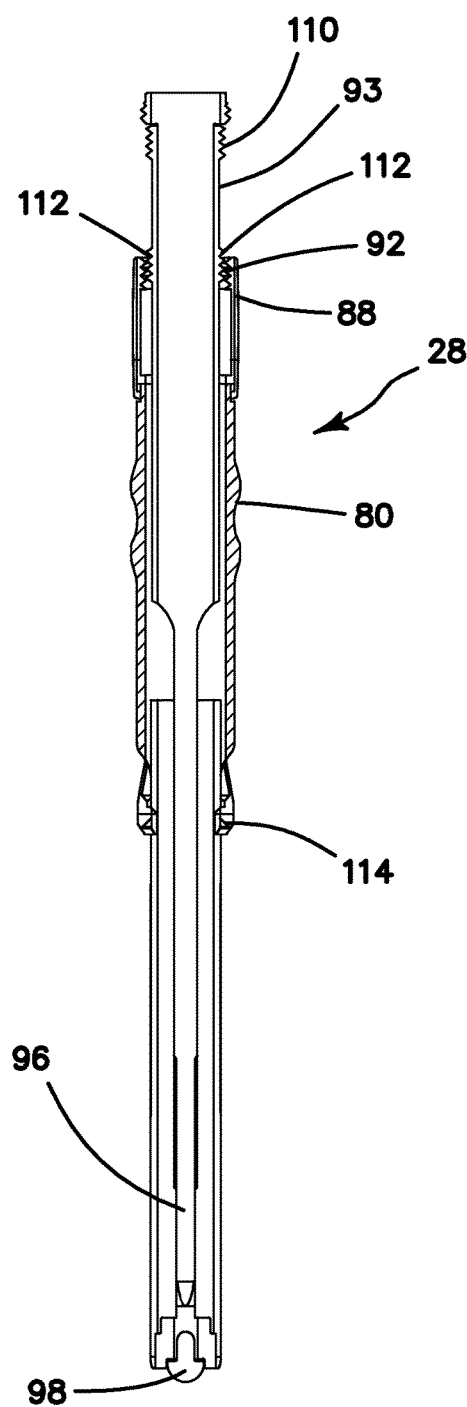
FIG. 18 is a cross-sectional view taken along line 18-18 of FIG. 16 of an instrument in a closed configuration according to the present invention.
Figure 15:
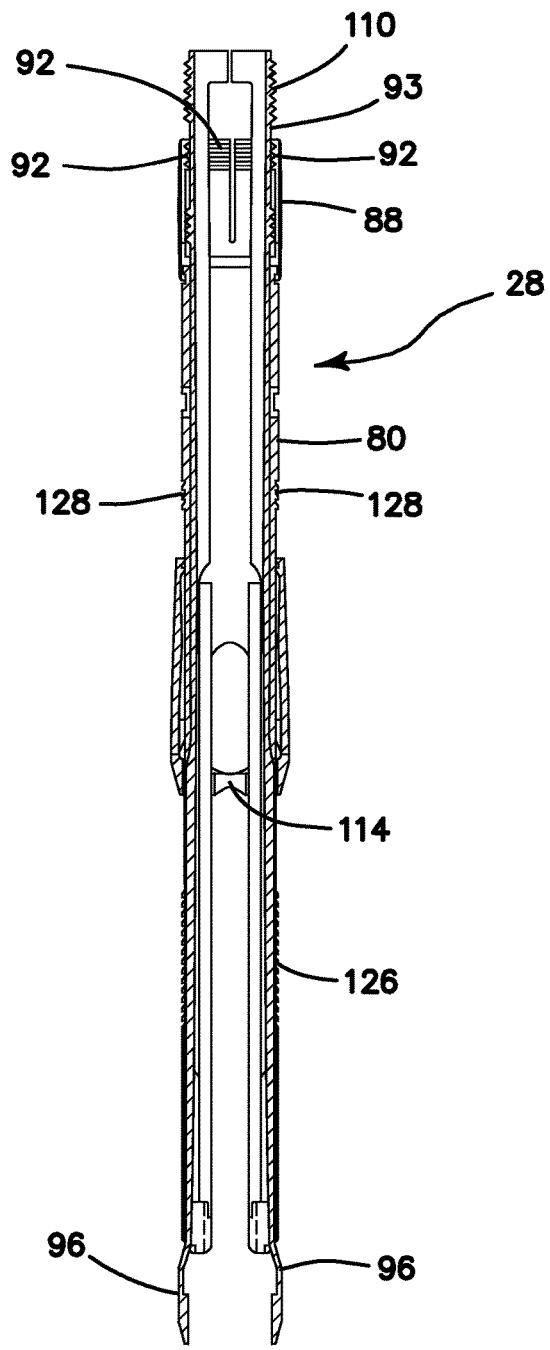
FIG. 15 is a cross-sectional view taken along line 15-15 of FIG. 13 of an instrument in an open configuration according to the present invention.
Figure 20:
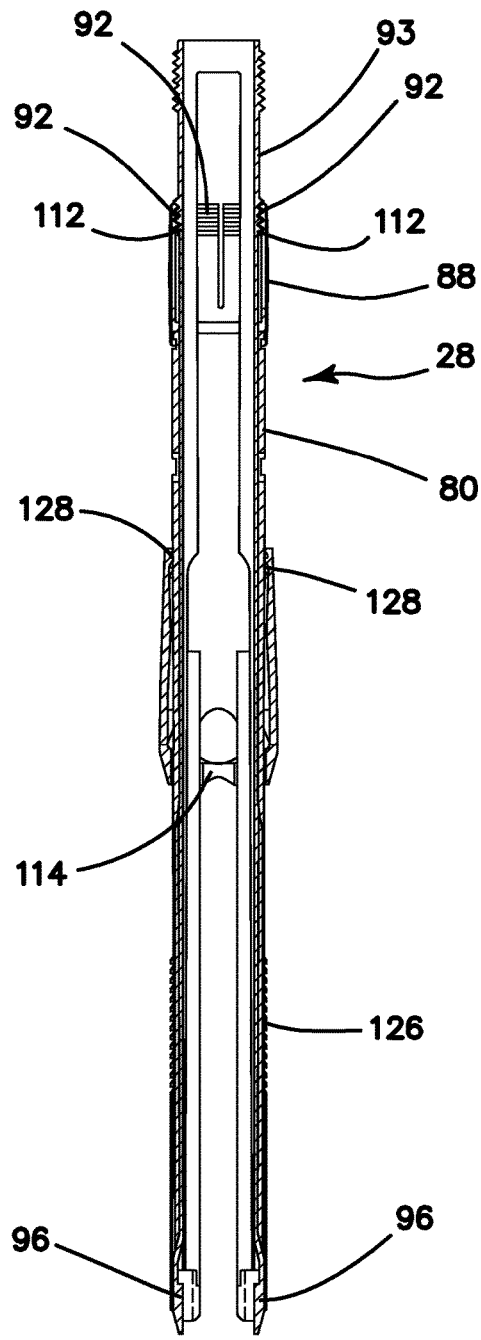
FIG. 20 is a cross-sectional view taken along line 20-20 of FIG. 17 of an instrument in a closed configuration according to the present invention.

Turning now to FIGS. 16-23, the instrument 28 includes a closed, locked configuration. In the closed, locked configuration, the tower 80 is positioned distally along the inner shaft 93 and the prongs 96 are flexed inwardly by the tower 80. The prongs 96 are at least partially contained inside the central lumen 82 of the tower 80 such that the prongs 96 are prevented from flexing outwardly to release from the receiver 24. In the locked configuration, the inner threads 92 of the knob 88 are located proximally to the second threaded section 112 such as visible in FIG. 17. In such a location, the tower 80 can easily slide proximally relative to the inner shaft 93 to the unlocked configuration releasing the prongs 96 from the central lumen 82 of the tower 80. Alternatively, the relative movement between the inner shaft 93 and the tower 80 can be arrested in the locked configuration by threading the inner threads 92 of the knob 88 to the second threaded section 112 as shown in FIGS. 18 and 20. FIGS. 22-23 illustrate the instrument 28 connected to the bone fixation system 20. In FIGS. 22-23, the tower 80 is in a closed, locked position with respect to the bone fixation system 20 in which the prongs 96 are flexed inwardly into recesses 60 on the receiver. FIGS. 22-23 show the second threaded section 112 in threaded connection with the knob 80. Hence, the closed configuration is also a locked configuration. Rotation of the knob 80 in an opposite direction would release the inner shaft 93 making it capable or moving into an open, unlocked configuration in which the prongs 96 splay away from the receiver 24 disconnecting from it.

With particular reference to FIG. 19, there is shown a close-up view of the distal end of the instrument 28 in a closed, locked configuration. Several features are noted in FIG. 19. In particular, the prong extension 98 at the distal end of the prong 96 is clearly visible. The first, second and third proximal surfaces 102, 106, 108 of the prong extension 98 that correspond to the first, second and third proximal surfaces 66, 68, 70 of the recess 60 are also noted. The enlarged wider portion 104 relative to the central portion 100 is also visible. Two hooks 86 are also shown in FIG. 19.

Figure 21:
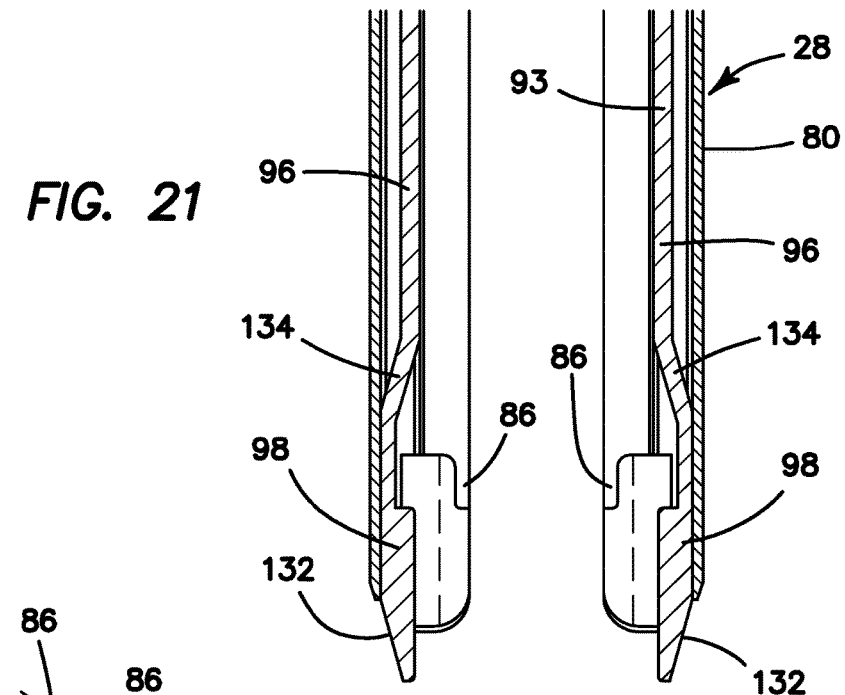
FIG. 21 is a sectional, detailed view of the distal end of the instrument of FIG. 20 according to the present invention.

Turning now to FIG. 21, there is shown an enlarged view of the distal end of the instrument 28 in a closed, locked configuration from another angle of view. The prong extensions 98 are provided with a taper 132. The taper 132 is an angled outer surface of the prong 96. The taper 132 advantageously prevents the instrument 28 and bone fixation system 20 from getting caught on nearby anatomy during insertion into a surgical site. The taper 132 advantageously makes the distal end at the receiver narrower and more capable of entering tight spaces without impingement upon the anatomy that may cause injury. Because the instrument 28 and bone fixation system 20 combination is less bulky in the lateral direction due to the taper 132, it is less likely for the instrument 28 to get hooked-up or leveraged against adjacent anatomy during insertion that may result in the dislodgement of the bone fixation system 20 from the instrument 28.

Still referencing FIG. 21, there is also shown an angled portion 134 of the prongs 96. The angled portion 134 advantageously provides a ramp surface for the tower 80 to slide against when moving distally over the prongs 96 from an open to a closed configuration. The two hooks 86 on the tower 80 are also shown in FIG. 21.

Figure 25:
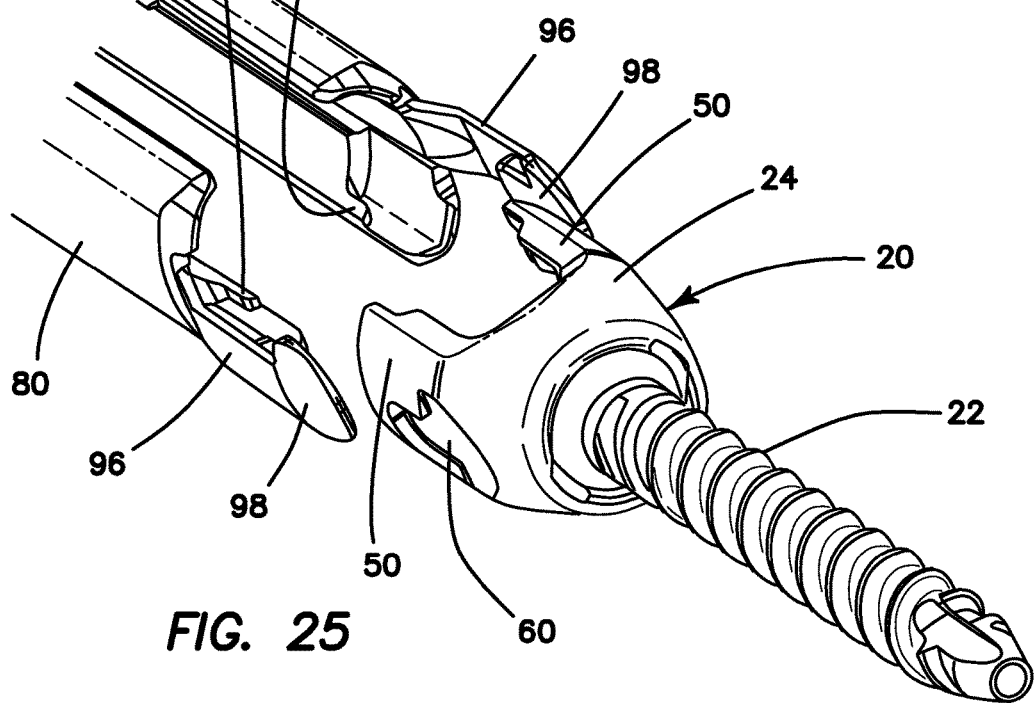
FIG. 25 is a partial bottom perspective view of an instrument and bone fixation system according to the present invention.
Figure 24:
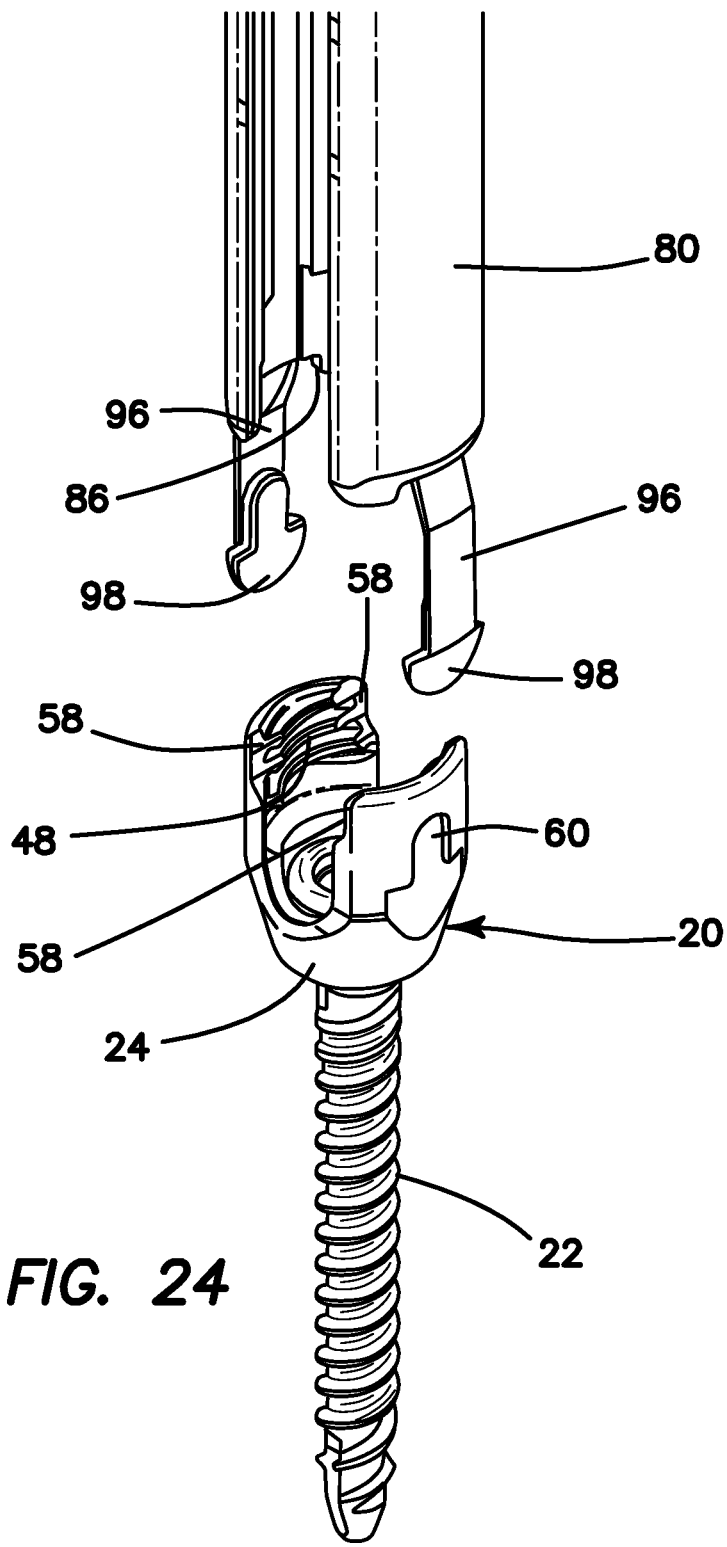
FIG. 24 is a partial top perspective view of an instrument and bone fixation system according to the present invention.
Figure 26:
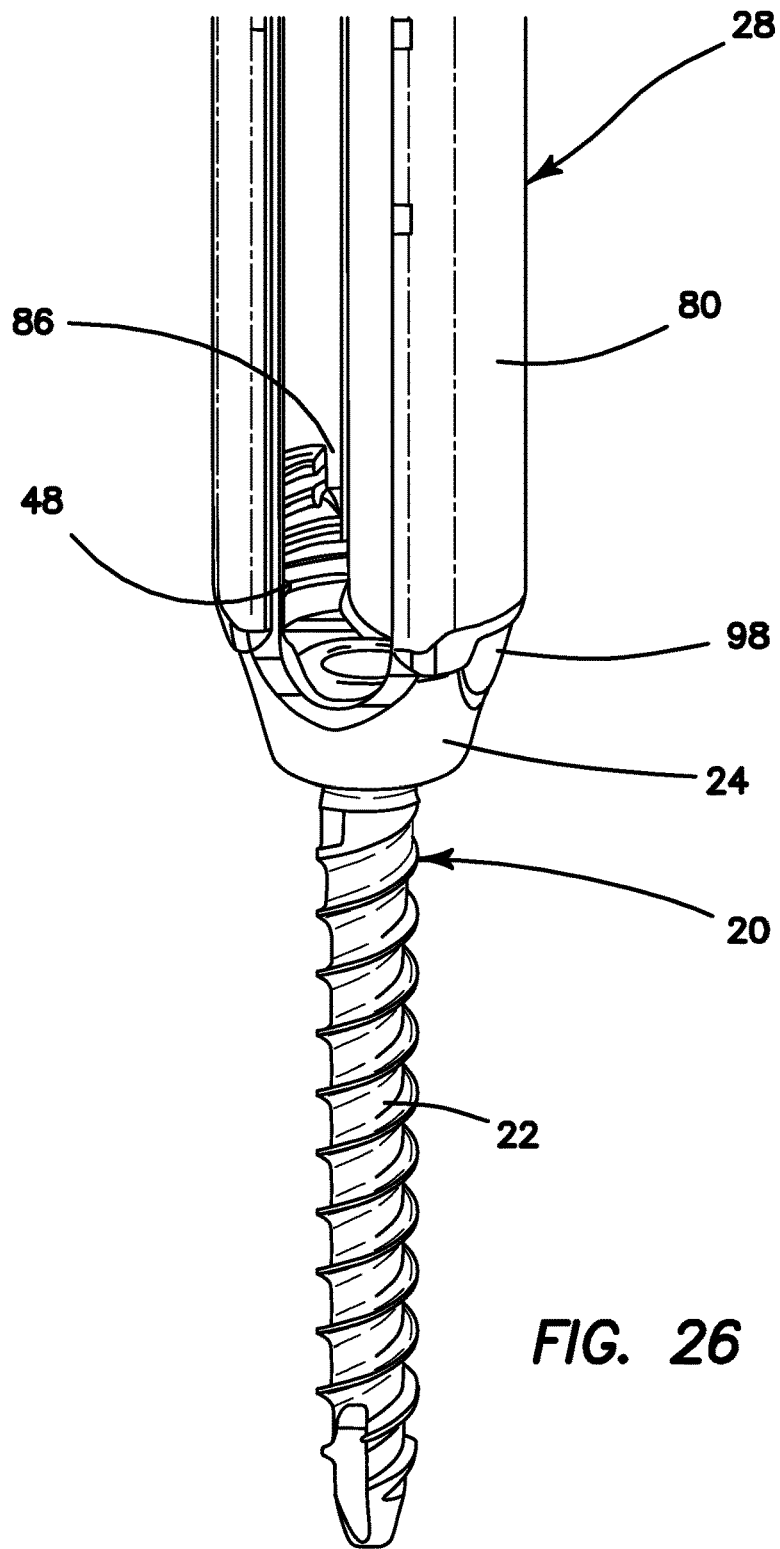
FIG. 26 is a partial top perspective view of an instrument and bone fixation system according to the present invention.

Turning now to FIGS. 24 and 25, in use, the instrument 28 is placed into an open, unlocked configuration with the prongs 96 extending distally and splaying out laterally. A bone fixation system 20 is approached as shown in FIGS. 24 and 25. The prongs 96 and their prong extensions 98 are placed in alignment with the arms 50 of the receiver 24 such that the prong extensions 98 are in juxtaposition with the recesses 60. When aligned, the tower 80 is moved distally relative to the inner shaft 93 flexing the prongs 96 into the recesses 60 on either side of the receiver 24. In the closed, locked configuration, the hooks 86 advantageously cover the smooth surfaces 58 on the inner surface of the receiver 24. The smooth surfaces 58 are flats or intersections of the threads 48 with a planar surface that cuts across a portion of the threads 48. FIG. 26 shows the hooks 86 covering, adjacent to, in juxtaposition, in contact with the smooth surfaces 58. With the instrument 28 loaded onto a bone fixation system 20, the knob 88 is turned to thread onto the second threaded section 112, thereby, locking the translation of the tower 80 to the inner shaft 93.

Figure 27C:
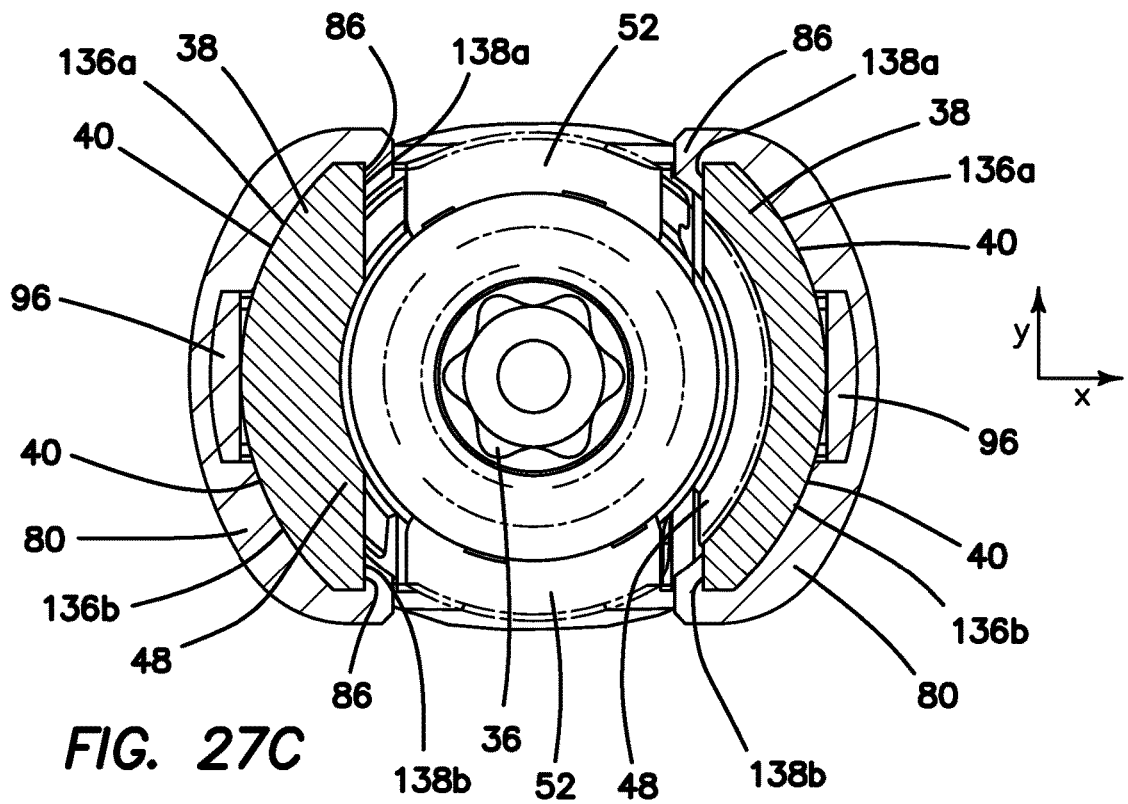
FIG. 27C is a cross-sectional view taken along line 27C-27C of FIG. 27A of an instrument and bone fixation system according to the present invention.

Turning now to FIGS. 27A-27C, there is shown various views of the bone fixation system 20 connected to the insertion instrument 28 while in a closed, locked configuration. In FIG. 27B, it can be seen that the hooks 86 cover or are in contact with at least a portion of the smooth surface flats 58 on the inner surface 42 of the receiver 24. This configuration of the instrument 24 and bone fixation system 20 combination advantageously provides for an extremely secure connection. In particular, as can be seen in FIG. 27C, at a cross-section taken above the location of prong extensions 98, the receiver 24 is secured by a first inner surface 136*a* of the tower 80 on one side of the prong 96 and a second inner surface 136*b* of the tower 80 on the other side of the prong 96 covering and/or in contact and/or juxtaposition with the outer surface 40 of the receiver 24. At the same cross-section, the hooks 86 provide a component parallel to the y-axis that secures the receiver 24 from the other side. In particular, the hooks 86 include an inner surface 138*a*, 138*b* covering and/or in contact and/or juxtaposition with the smooth surface flats 58 of the inner surface 42 of the receiver 24. The inner surface 138*a* of a hook 86 includes a component parallel to the y-axis that is opposite to or spaced apart from the component parallel to y-axis of the first inner surface 136*a* of the tower 80 capturing a portion of the sidewall 38 of the receiver 24 therebetween in the location of the smooth surface flats 58. Similarly the inner surface 138*b* of a hook includes a component parallel to the y-axis that is opposite to or spaced apart from the component parallel to the y-axis of the second inner surface 136*b* of the tower 80 capturing a portion of the sidewall 38 of the receiver 24 therebetween in the location of the smooth surface flats 58. Hence, at the cross-sectional location or longitudinal level shown in FIG. 27C, that is, at a location above the prong extensions 98, each arm 50 of the receiver 24 is secured to the instrument 28 by the inner surface 138*a* of a first hook 86 and inner surface 136*a* of the tower 80 at one end and by the inner surface 138*b* of a second hook 86 and inner surface 136*b* of the tower 80 at the other end of the arm 50. This configuration is repeated for the other arm 50 providing eight surface contact points in total which secures the tower 80 to the receiver 24. Each arm 50 of the receiver 24 is secured by four points of contact or potential contact. In other words, each arm 50 of the receiver 24 is captured between the first inner surface 136*a* and second inner surface 136*b* and a first inner surface 138*a* and second inner surface 138*b* of two hooks 86.

Figure 28C:
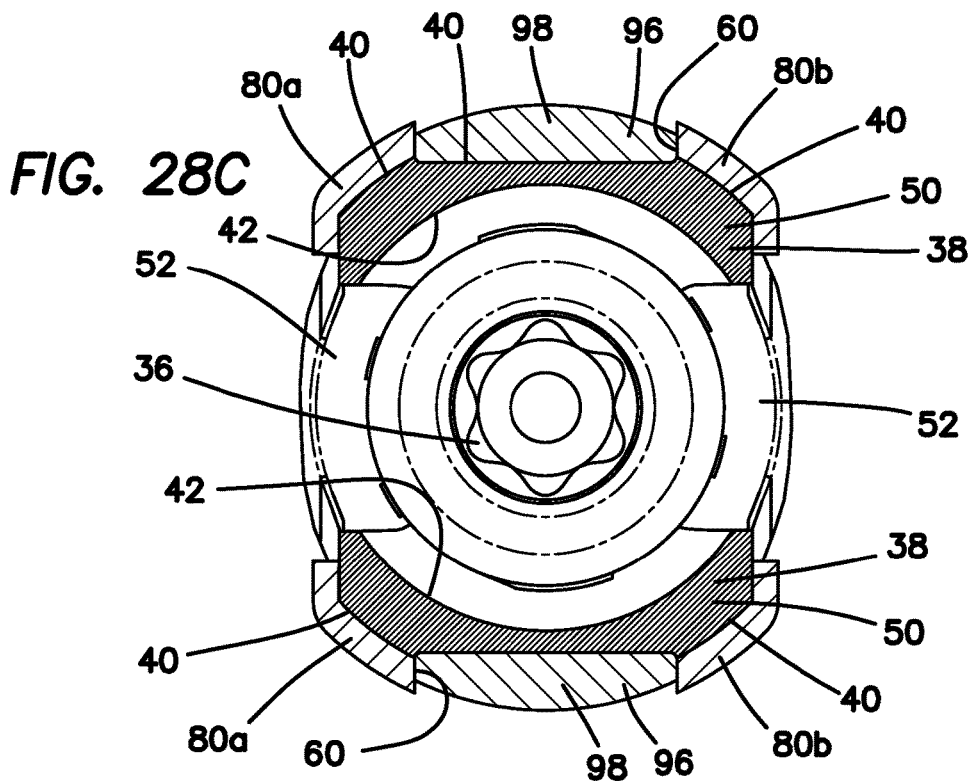
FIG. 28C is a cross-sectional view taken along line 28C-28C of FIG. 28A of an instrument and bone fixation system according to the present invention.
Figure 28A:
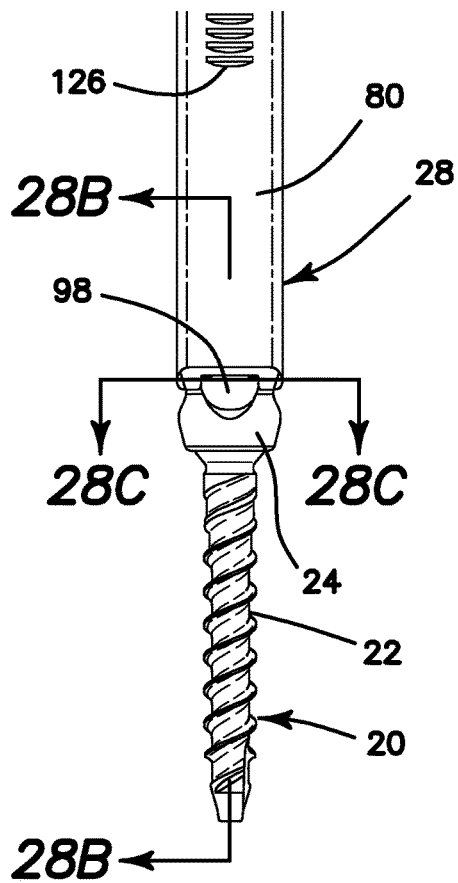
FIG. 28A is a partial side elevational view of an instrument and bone fixation system according to the present invention.
Figure 28B:
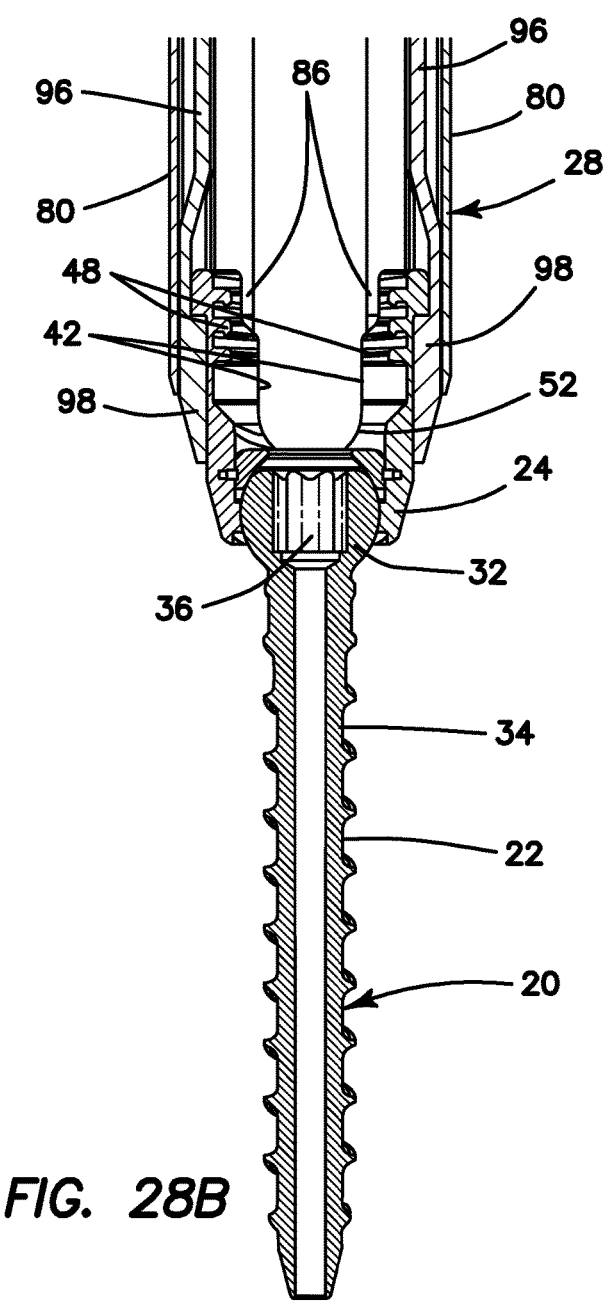
FIG. 28B is a cross-sectional view taken along line 28B-28B of FIG. 28A of an instrument and bone fixation system according to the present invention.

Turning now to FIGS. 28A-28C, there is shown various views of the bone fixation system 20 connected to the insertion instrument 28 while in a closed, locked configuration. In FIG. 28B, it can be seen that the hooks 86 cover at least a portion of the smooth surface flats 58 on the inner surface 42 of the receiver 24 without extending into the channels 52. The instrument 28 advantageously grabs the sidewall 38 of the receiver 24 from the inside as well as from the outside without impinging into the channel 52 location of the receiver 24, thereby, advantageously keeping the working channel for the insertion of the connecting rod 30, set screw 26 and other driver instruments that would engage the driver connection socket 36 on the head 32 of the screw 22 clear from interference from the instrument 28. As can be seen in FIG. 28C, at a cross-section through or at the prong extensions 98, the prong extensions 98 are resident inside the recesses 60. At this cross-sectional level relative to the longitudinal axis, the receiver 24 is secured by the oppositely disposed prong extensions 98 in contact with each arm 50. Not only do the prong extensions 98 secure the receiver 24 at this cross-sectional longitudinal level, but also, the inner surface of the tower 80 engages the outer surface 40 of the sidewall 38 in two locations 80a and 80b at each arm 50. In contrast with the cross-sectional level shown in FIG. 27C, there is no securement of the inner surface 42 of the sidewall 38 because the cross-section is taken beneath the location of the hooks 86.

With reference back to FIGS. 3 and 19, the prong extension 98 of FIG. 19 is complementary in shape and size to be inserted and fit securely within a similarly-shaped recess 60. Both the prong extension 98 and the complementary recess 60 include four lateral surfaces. In traditional screw systems, the prong extension is typically circular in shape and it corresponds to a circular-shaped recess. Alternatively, an elongated prong extension is typically provided having a major axis parallel to the longitudinal axis of the screw. In either case, the prong extension 98 and the corresponding recess include a component that is lateral to the longitudinal axis of the screw. In particular, three lateral components are provided that are spaced apart along the longitudinal axis.

Figure 29A:
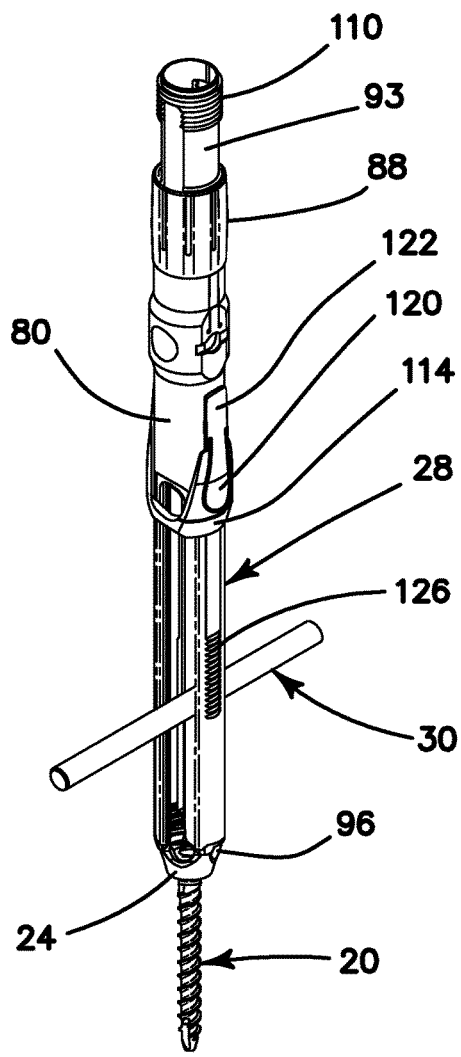
FIG. 29A is a top perspective view of an instrument, connecting rod and bone fixation system according to the present invention.
Figure 29B:
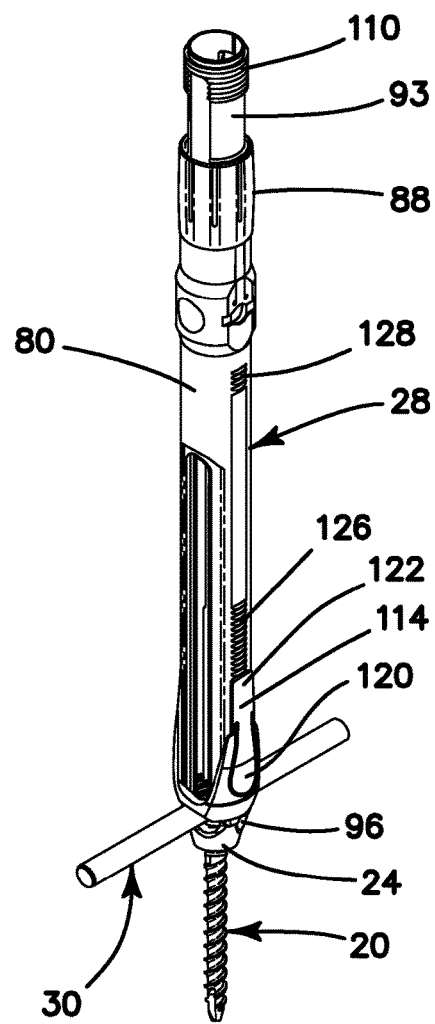
FIG. 29B is a top perspective view of an instrument, connecting rod and bone fixation system according to the present invention.

In use, with the instrument 28 connected to the bone fixation system 20, the combination is inserted into the surgical site. When in position, the bone fastener 22 is placed into bone by locking the polyaxial angulation of the bone fastener 22 relative to the receiver 24 with another instrument inserted in through central lumen of the instrument 28 and then turning the instrument 28 to drive the bone fastener 22 into bone. Alternatively, another instrument is inserted through the central lumen of the instrument 28 to engage the driver connection socket 36 on the head 32 of the fastener 22. The bone fastener 22 is then driven into bone by rotating the other instrument relative to the receiver 24. With the bone fastener 22 positioned in the desired anatomical location, a connecting rod 30 is placed inside the channel 52. Sometimes due to variations in the bony anatomy, the connecting rod 52 will be positioned high inside the channel 52 or not even within the receiver 24 as shown in FIG. 29A. The reducer 114 is then easily pushed from a proximal location as shown in FIG. 29A to a distal location as shown in FIG. 29B pushing the connecting rod 30 into position, thereby, reducing the distance between the connecting rod 30 and the seat of the receiver 24. FIG. 29B illustrates the proximal ends 122 of fingers 118 engaged with the first rack 126 such that the one or more tooth 124 on the fingers 118 is locked into the first rack 126 preventing proximal translation of the reducer 114. The present invention advantageously permits the reducer 114 to remain locked with respect to the tower 80 in the location of the first rack 126 such that proximal translation of the reducer 114 is prevented by the teeth 124 yet distal translation is permitted by simply pushing the reducer 114 in the distal direction. The teeth on the first rack 126 and the teeth 124 on the fingers 118 are configured such that distal movement of the reducer 114 is permitted as the teeth 124 of the reducer 114 ramp over the teeth on the first rack 126. This configuration advantageously permits easy reduction of the distance between the connecting rod 30 and the seat of the receiver 24. A fully reduced and seated connecting rod 30 is shown in FIG. 29B. With the rod 30 seated, a set screw 26 is inserted in through the proximal end of the instrument 28 through the central lumen and threaded into the threads 48 of the receiver 24 capturing the connecting rod 30 between the set screw 26 and the receiver 24 and at the same time locking the angulation of the bone fastener 22 relative to the receiver 24. At this point, with all of the bone fixation systems 20 and rods 30 secured, the instrument 28 is removed by turning the knob 88 to unlock the inner shaft 93 relative to tower 80 and sliding the tower 80 proximally to release the prongs 96 from the receiver 24. The instrument 28 is then removed from the surgical site.

Throughout this specification wherever threads, threaded portions or threaded engagements are mentioned, it is to be understood by one skilled in the art that the invention is not so limited and any coupling, locking or interlocking surface or mechanism known to one skilled in the art may be alternatively employed. For example, threaded engagement, twist-lock, snap-fit, friction fit, press-fit, ratcheting mechanism, or any friction locking system is within the scope of the present invention and may be substituted wherever such substitution is possible.

It will be understood that many modifications can be made to the various disclosed embodiments without departing from the spirit and scope of the concept. For example, various sizes of the surgical devices are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention.

We claim:

1. A bone fixation system, comprising:
   a bone fastener including:
      a bone engaging portion; and
      a head connected to the bone engaging portion;
   a receiver having a proximal end, a distal end and a longitudinal axis; the receiver including:
      a sidewall extending between the proximal end and the distal end and having an inner surface and an outer surface;
      an inner bore extending between a top opening at the proximal end and a bottom opening at the distal end; the bone fastener being connected to the receiver such that the bone engaging portion extends through the bottom opening;
      two oppositely disposed arms defined by the sidewall and at least one rod channel defined between the two arms; the at least one rod channel being interconnected with the top opening and the inner bore; the inner surface of each arm having a longitudinally extending interlocking surface located between two longitudinally extending smooth surfaces; each smooth surface extends from the outer surface to the inner surface; the longitudinally extending portion of the smooth surfaces being configured to engage with an insertion instrument;
   wherein the two longitudinally extending smooth surfaces of one arm are parallel to the two longitudinally extending smooth surfaces of the opposite arm; and
   wherein the smooth surfaces of each arm are formed into the interlocking surface.

2. The bone fixation system of claim 1 wherein the two longitudinally extending smooth surfaces of one arm lie along a chord of a cross-section taken perpendicular to the longitudinal axis; the chord intersecting the inner surface of the arm in two locations.

3. The bone fixation system of claim 1 wherein the smooth surfaces of one arm are located opposite from the smooth surfaces of the other arm.

4. The bone fixation system of claim 1 further including an insertion instrument configured to releasably connect to the two smooth surfaces and at least one location on the outer surface of the receiver of each arm.

5. The bone fixation system of claim 4 wherein the insertion instrument includes two oppositely disposed prongs having an open configuration and a closed configuration; wherein in the open configuration the distance between the distal ends of the prongs is greater than in the closed configuration; the prongs being configured to engage and connect to recesses formed in the outer surface of the receiver in the closed configuration.

6. The bone fixation system of claim 1 further including a locking cap located between the arms of the receiver and having an interlocking outer surface configured to interlock with the interlocking inner surface of the arms of the receiver; wherein the locking cap is configured to capture a connecting element inside the channel between the locking cap and receiver.

7. The bone fixation system of claim 1 wherein the smooth surfaces of each arm extend from the outer surface to the interlocking surface.

8. A bone fixation system, comprising:
a bone fastener including:
a bone engaging portion; and
a head integrally connected to the bone engaging portion;
a receiver having a proximal end, a distal end and a longitudinal axis; the receiver including:
a sidewall extending between the proximal end and the distal end and having an inner surface and an outer surface;
an inner bore extending between a top opening at the proximal end and a bottom opening at the distal end; the bone fastener being connected to the receiver such that the bone engaging portion extends through the bottom opening;
two oppositely disposed arms defined by the sidewall and at least one rod channel defined between the two arms; the at least one rod channel being interconnected with the top opening and the inner bore; the inner surface of each arm having a longitudinally extending interlocking inner surface;
a recess formed in the outer surface of each arm; each recess extending inwardly from the outer surface to define a recessed floor surface having a perimeter surface perpendicular to the floor surface; the perimeter surface having a first proximal surface, interconnected to a second proximal surface and a third proximal surface; the first proximal surface, second proximal surface and third proximal surface having a lateral dimension perpendicular to the longitudinal axis; wherein the first proximal surface is located in between and proximal to the second proximal surface and third proximal surface along the longitudinal axis; wherein the first proximal surface is connected to the second proximal surface by a first side surface and the first proximal surface is connected to the third proximal surface by a second side surface; wherein the first side surface and the second side surface together with the first proximal surface define an elongate central portion; wherein the second proximal surface and the third proximal surface are located on either side of the central portion and each extends laterally to the longitudinal axis; wherein the first and second side surfaces are parallel to the longitudinal axis to prevent lateral movement of the receiver when engaged to an insertion instrument.

9. The bone fixation system of claim 8 wherein the perimeter surface of each recess includes a distal surface; wherein the elongate central portion of the recess is interconnected with a wider distal portion comprising the second proximal surface, the third proximal surface and a distal surface; the second proximal surface being interconnected to the third proximal surface by the distal surface.

10. The bone fixation system of claim 8 wherein the perimeter surface extends radially inwardly.

11. The bone fixation system of claim 8 further including an insertion instrument having two oppositely disposed prongs having prong extensions configured to be inserted into the oppositely disposed recesses to attach the bone fixation system to the insertion instrument; wherein the each prong extension includes a first proximal surface, a second proximal surface and a third proximal surface that correspond to the first proximal surface, second proximal surface and third proximal surface of each recess.

12. A bone fixation system, comprising:
a bone fastener including:
a bone engaging portion; and
a head connected to the bone engaging portion;
a receiver having a proximal end, a distal end and a longitudinal axis; the receiver including:
a sidewall extending between the proximal end and the distal end and having an inner surface and an outer surface;
an inner bore extending between a top opening at the proximal end and a bottom opening at the distal end; the bone fastener being connected to the receiver such that the bone engaging portion extends through the bottom opening;
a first arm oppositely disposed from a second arm; the first and second arms being defined by the sidewall; at least one rod channel being defined between the two arms; the at least one rod channel being interconnected with the top opening and the inner bore; the inner surface of each arm having two flat surfaces interconnected by a longitudinally extending threaded surface; the flat surfaces being located near the proximal end of the receiver; a recess formed in the outer surface of each arm; each recess extending inwardly from the outer surface to define a recessed floor surface; and
an instrument comprising an elongate tower having a central lumen extending between a proximal end and an open distal end; the distal end of the tower having four hooks and two prong extensions; two of the hooks being configured to contact the two flat surfaces and one prong extension being configured to contact the floor surface on the first arm and the other two hooks being configured to contact the two flat surfaces and one prong extension being configured to contact the floor surface on the second arm;
wherein the two flat surfaces of the first arm are parallel to the floor surface of the first arm and the two flat surfaces of the second arm are parallel to the floor surface of the second arm;
wherein the flat surfaces are formed into the threads and extend from the outer surface to the threaded surface.

13. The bone fixation system of claim 12 wherein each arm is defined by the outer surface interconnected to the inner surface.

14. The bone fixation system of claim 12 wherein each hook extends around the edge of the arm to contact the flat surfaces without extending into the inner bore.

15. The bone fixation system of claim 12 wherein the outer surface of receiver includes two oppositely disposed recesses; each recesses having three separated perimeter surfaces; each perimeter surface being perpendicular to the longitudinal axis.

16. The bone fixation system of claim 15 wherein the instrument includes an inner shaft having two distally extending and oppositely disposed prongs; each prong having a prong extension configured to be inserted into the oppositely disposed recesses and contact the three separated perimeter surfaces.

17. The bone fixation system of claim 12 wherein each prong extension includes an angled portion.

* * * * *